United States Patent [19]

Paioni

[11] 4,320,137
[45] Mar. 16, 1982

[54] DERIVATIVES OF PERHYDRO-AZA-HETEROCYCLES

[75] Inventor: Romeo Paioni, Reinach, Switzerland

[73] Assignee: Ciba-Geigy Corporation, Ardsley, N.Y.

[21] Appl. No.: 183,482

[22] Filed: Sep. 28, 1980

Related U.S. Application Data

[62] Division of Ser. No. 27,337, Apr. 5, 1979, Pat. No. 4,246,269, which is a division of Ser. No. 827,274, Aug. 24, 1977, Pat. No. 4,160,837.

[30] Foreign Application Priority Data

Sep. 1, 1976 [LU] Luxembourg ............................ 75701

[51] Int. Cl.$^3$ .................... C07D 207/12; A61K 31/40
[52] U.S. Cl. ............................... 424/274; 260/326.33; 260/326.47; 260/326.5 C; 260/326.5 M
[58] Field of Search ........................ 260/326.33, 326.47, 260/326.5 C, 326.5 M; 424/274

[56] References Cited

U.S. PATENT DOCUMENTS

| | | | |
|---|---|---|---|
| 3,381,013 | 4/1968 | Minor | 260/326.5 M |
| 3,446,897 | 5/1969 | Koppanyi | 424/274 |
| 3,577,432 | 5/1971 | Helsley | 260/326.5 M |
| 3,627,766 | 12/1971 | Eichenberger et al. | 424/251 |
| 3,823,151 | 7/1974 | Eichenberger et al. | 424/263 |
| 3,961,959 | 6/1976 | Fujiwhara et al. | |
| 4,160,837 | 7/1979 | Paioni | 424/267 |
| 4,246,269 | 1/1981 | Paioni | 260/326.47 |
| 4,251,541 | 2/1981 | Walsh | 260/326.47 |

FOREIGN PATENT DOCUMENTS

| | | |
|---|---|---|
| 1964515 | 7/1970 | Fed. Rep. of Germany . |
| 3000623 | 7/1980 | Fed. Rep. of Germany . |
| 3000624 | 7/1980 | Fed. Rep. of Germany . |
| 3000625 | 7/1980 | Fed. Rep. of Germany . |
| 7620260 | 1/1977 | France . |
| 511874 | 10/1971 | Switzerland . |
| 2040933 | 9/1980 | United Kingdom ........ 260/326.5 M |

OTHER PUBLICATIONS

Chemical Abstracts 88:P152446e, Paioni, (1978).

Primary Examiner—Mary C. Lee
Attorney, Agent, or Firm—Prabodh I. Almaula

[57] ABSTRACT

The present invention provides new derivatives of perhydro-aza-heterocycles of the formula

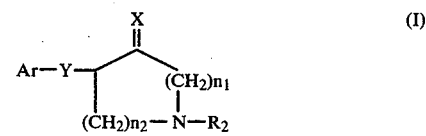

in which X is the oxo radical or hydrogen and the radical OR$_1$, in which R$_1$ is hydrogen or a substituted or unsubstituted aliphatic hydrocarbon radical, a substituted or unsubstituted araliphatic hydrocarbon radical or a substituted or unsubstituted aromatic hydrocarbon radical or an acyl radical, R$_2$ is hydrogen or a substituted or unsubstituted aliphatic hydrocarbon radical, Y is oxygen or sulphur, n$_1$ and n$_2$ each are values of 1 to 3, n$_1$+n$_2$ being at most four, and Ar is a substituted or unsubstituted aromatic hydrocarbon radical, and the acid addition salts, in particular the pharmaceutically acceptable acid addition salts thereof. These new substances possess valuable pharmacological properties, in particular antidepressant activity, and can be used for the treatment of mental depressions. Specific embodiments are trans- and cis-3-hydroxy-4-(3,4-dimethyl-phenoxy)-piperidine, trans- und cis-3-hydroxy-4-(2,3-dimethyl-phenoxy)-piperidine, their 1-methyl derivatives and the pharmaceutically acceptable salts of these substances.

16 Claims, No Drawings

DERIVATIVES OF PERHYDRO-AZA-HETEROCYCLES

This is a division of application Ser. No. 027,337 filed Apr. 5, 1979, now U.S. Pat. No. 4,246,269, which in turn is a divisional of application Ser. No. 827,274, filed Aug. 24, 1977, now U.S. Pat. No. 4,160,837.

The present invention relates to new derivatives of perhydro-aza-heterocycles and their salts, processes for their production, pharmaceutical compositions which contain the new compounds and the pharmaceutical use of these compositions.

The compounds according to the invention correspond to the formula

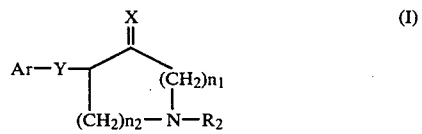

in which X is the oxo radical or hydrogen and the radical $OR_1$, in which $R_1$ is hydrogen or a substituted or unsubstituted aliphatic hydrocarbon radical, a substituted or unsubstituted araliphatic hydrocarbon radical or a substituted or unsubstituted aromatic hydrocarbon radical or an acyl radical, $R_2$ is hydrogen or a substituted or unsubstituted aliphatic hydrocarbon radical, Y is oxygen or sulphur, $n_1$ and $n_2$ each are values of 1 to 3, $n_1+n_2$ being at most four, and Ar is a substituted or unsubstituted aromatic hydrocarbon radical.

Aliphatic hydrocarbon radicals $R_1$ and $R_2$ are, in particular, lower alkyl but can also be lower alkenyl or lower alkynyl.

Araliphatic hydrocarbon radicals are, especially, phenyl-lower alkyl and also phenyl lower-alkenyl or phenyl lower-alkynyl.

Aromatic hydrocarbon radicals are, especially, phenyl and also naphthyl, such as 1- or 2-naphthyl, hydrogenated naphthyl, such as 5,6,7,8-tetrahydro-1-naphthyl or 5,6,7,8-tetrahydro-2-naphthyl, anthryl, such as 1-, 2- or 9-anthryl, 9,10-dihydro-9,10-ethanoanthracenyl, such as 9,10-dihydro-9,10-ethanoanthracen-1-yl, or 9,10-dihydro-9,10-ethenoanthracenyl, such as 9,10-dihydro-9,10-ethenoanthracen-1-yl, -2-yl or -9-yl. Substituents in the phenyl part of phenyl-lower alkyl, phenyl-lower alkenyl and phenyl-lower alkynyl, or in an aromatic ring of naphthyl of the indicated type or in one or two aromatic rings of anthryl, 9,10-dihydro-9,10-ethanoanthracenyl or 9,10-dihydro-9,10-ethenoanthracenyl, in each case of the type indicated above, are, for example, lower alkyl which is unsubstituted or substituted, such as by halogen, such as lower alkyl or trifluoromethyl, free, etherified or esterified hydroxyl, such as hydroxyl, lower alkoxy, methylenedioxy or halogen, and/or free or functionally modified carboxyl, such as carboxyl, esterified carboxyl, for example lower alkoxycarbonyl, or amidated carboxyl, for example unsubstituted or N-substituted carbamoyl, such as carbamoyl, N-lower alkylcarbamoyl or N,N-dilower alkyl-carbamoyl, and also, for example, nitro or cyano, it being possible for there to be, in each case, 1, 2 or 3 of the indicated radicals present and for these radicals to be either identical or different from one another and for substituted radicals to carry one or more substituents in any of the positions suitable for substitution.

Substituents of lower alkyl and also of lower alkenyl and lower alkynyl are, for example, free, etherified or esterified hydroxyl, such as hydroxyl, lower alkoxy, phenoxy and/or halogen, or free or functionally modified carboxyl, such as carboxyl, esterified carboxyl, for example lower alkoxycarbonyl, or amidated carboxyl, for example carbamoyl, N-lower alkyl-carbamoyl or N,N-di-lower alkyl-carbamoyl, or cyano.

In the context of the present invention, radicals and compounds designated as "lower" contain preferably up to 7 and especially up to 4 carbon atoms and acyl radicals contain up to 5 carbon atoms.

The general terms used in the context of the present invention are, for example, as defined below:

Lower alkyl can be unbranched or branched, especially on the α-carbon atom, and is, for example, methyl, ethyl, propyl, isopropyl, n-butyl, isobutyl, sec.-butyl or tert.-butyl.

Lower alkenyl contains one or more double bonds and is, for example, allyl, 1- or 2-methylallyl or 3,3-dimethylallyl, whilst lower alkynyl is, for example, propargyl.

Phenyl-lower alkyl is, for example, benzyl or 1- or 2-phenylethyl, whilst phenyl-lower alkenyl is, for example, cinnamyl and phenyl-lower alkynyl is, for example, 3-phenylpropargyl and the radical $R_1$ can, for example, also be styryl or phenylethynyl.

Lower alkoxy is, for example, methoxy, ethoxy, n-propyloxy, isopropyloxy, n-butyloxy, isobutyloxy, sec.-butyloxy or tert.-butyloxy and also n-pentyloxy or neopentyloxy.

Halogen is especially chlorine or bromine but can also be fluorine and, furthermore, iodine.

Lower alkoxy-carbonyl is, for example, methoxycarbonyl or ethoxycarbonyl, whilst N-lower alkyl-carbamoyl and N,N-dilower alkyl-carbamoyl are, for example, N-methylcarbamoyl, N,N-dimethylcarbamoyl, N-ethylcarbamoyl, N-ethyl-N-methyl-carbamoyl or N,N-diethylcarbamoyl.

Lower alkoxy-lower alkyl is, for example, methoxymethyl, ethoxymethyl, 2-methoxyethyl, 2-ethoxyethyl, 1-methoxy-2-propyl, 1-ethoxy-2-propyl or 1-ethoxy-2-butyl and lower alkoxy is separated from the linking carbon atom of the lower alkyl part preferably by at least 2 and usually by 2–3 carbon atoms.

Phenoxy-lower alkyl is, for example, phenoxymethyl or especially 2-phenoxyethyl and phenyl in such radicals, for example as an aromatic radical in an araliphatic group $R_1$, can be substituted.

Halogeno-lower alkyl is, for example, fluoromethyl, trifluoromethyl, chloromethyl, dichloromethyl, trichloromethyl, 2-chloroethyl or 2-bromoethyl.

Carboxy-lower alkyl is, for example, carboxymethyl, 2-carboxyethyl or 1-carboxy-2-propyl, whilst lower alkoxycarbonyl-lower alkyl is, for example, methoxycarbonylmethyl, 2-methoxycarbonylethyl, 1-methoxycarbonyl-2-propyl, 1-ethoxycarbonyl-2-butyl, 1-ethoxycarbonyl-3-butyl, 2-ethoxycarbonylethyl or 1-ethoxycarbonyl-2-propyl.

Unsubstituted or N-substituted carbamoyl-lower alkyl is, for example, carbamoylmethyl, carbamoylethyl, 1-carbamoyl-2-propyl, N-methylcarbamoylmethyl, N-ethylcarbamoylmethyl, N,N-dimethylcarbamoylmethyl, 2-N-methylcarbamoylethyl, 2-N-ethylcarbamoyl-ethyl, 2-N,N-dimethylcarbamoylethyl, 1-N-methylcarbamoyl-2-propyl or 1-N,N-dimethylcarbamoyl-2-propyl.

Cyano-lower alkyl is, for example, cyanomethyl, 1- or 2-cyanoethyl, 3-cyanopropyl and 1-cyano-2-propyl.

Acyl radicals $R_1$ correspond to the formula —C(=O)—R, in which R is a substituted or unsubstituted aliphatic, cycloaliphatic, aromatic or araliphatic hydrocarbon radical, such as substituted or unsubstituted lower alkyl and also lower alkenyl or lower alkynyl, substituted or unsubstituted monocyclic or polycyclic cycloalkyl, substituted or unsubstituted phenyl or phenyl-lower alkyl and also phenyl-lower alkenyl or phenyl-lower alkynyl. Substituents of lower alkyl and also lower alkenyl or lower alkynyl are, for example, free, etherified or esterified hydroxyl, such as hydroxyl, lower alkoxy and/or halogen, and substituents of cycloalkyl, phenyl, phenyl-lower alkyl, phenyl-lower alkenyl and phenyl-lower alkynyl are lower alkyl which is unsubstituted or substituted, for example by halogen, such as lower alkyl or trifluoromethyl, free, etherified or esterified hydroxyl, such as hydroxyl, lower alkoxy or halogen, and/or functionally modified carboxyl, such as esterified carboxyl, for example lower alkoxycarbonyl, or amidated carboxyl, for example carbamoyl, N-lower alkylcarbamoyl or N,N-di-lower alkyl-carbamoyl, or cyano, and substituted radicals can carry one or more substituents in any of the positions suitable for substitution.

Monocyclic cycloalkyl is, for example, cyclopropyl, cyclopentyl or cyclohexyl, whilst polycyclic cycloalkyl is, for example, bicyclo[2.2.1]heptyl (norbornyl), bicyclo[2.2.2]octyl or adamantyl, such as 1-adamantyl.

Salts of compounds of the formula I are acid addition salts, especially pharmaceutically acceptable, non-toxic acid addition salts with suitable inorganic acids, for example hydrochloric acid, hydrobromic acid, sulphuric acid or phosphonic acid, or with suitable organic acids, such as aliphatic, cycloaliphatic, aromatic, araliphatic or heterocyclic carboxylic or sulphonic acids, for example formic acid, acetic acid, propionic acid, succinic acid, glycolic acid, lactic acid, malic acid, tartaric acid, citric acid, ascorbic acid, maleic acid, fumaric acid, pyruvic acid, benzoic acid, anthranilic acid, 4-hydroxybenzoic acid, salicylic acid, phenylacetic acid, embonic acid, methanesulphonic acid, ethanesulphonic acid, hydroxyethanesulphonic acid, ethylenesulphonic acid, 4-chlorobenzenesulphonic acid, toluenesulphonic acid, naphthalenesulphonic acid, sulphanilic acid or cyclohexylaminesulphonic acid. Because of the close relationships between the novel compounds in the free form and in the form of their salts, the free compounds and the salts are, where appropriate, also to be understood to include the corresponding salts and, respectively, the free compounds, in respect of general sense and intended use.

The compounds of the present invention can be in the form of mixtures of isomers, for example of mixtures of compounds of the cis- and trans-configuration, or of single isomers, for example of the cis-configuration or of the transconfiguration, and also in the form of racemates or optical antipodes.

The new compounds of the general formula I have valuable pharmacological properties; in particular, they possess anti-depressant activities, which can be demonstrated with the aid of corresponding pharmacological tests. Thus, these substances effect inhibition of the absorption of noradrenaline, as can be shown, for example, by means of their inhibition of the depletion of noradrenaline effected by 3-hydroxy-4-methyl-$\alpha$-methyl-phenethylamine in the brains of rats [A. CARLSSON, H. CORRODI, K. FUXE and T. HOEKFELT: Europ. J. Pharmacol. 5, 367 (1969)] after peroral administration of 100 mg/kg. Furthermore, they effect potentiation of serotoninergic effects, which can be demonstrated by means of their potentiation of the tremor capitis induced by 5-hydroxytryptophane in mice after intraperitoneal administration of 3 to 100 mg/kg. A particular characteristic of these substances is inhibition of the absorption of serotonin, as can be shown by means of their inhibition of the depletion of serotonin effected by 2-hydroxy-4-methyl-$\alpha$-ethyl-phenethylamine [A. CARLSSON et al.: Europ. J. Pharmacol. 5, 357 (1969)] in the brains of rats after peroral administration of doses of 3 to 100 mg/kg.

These pharmacological properties characterise the new compounds and their pharmaceutically acceptable acid addition salts as anti-depressants, which can be used, in the form of pharmaceutical compositions, for the treatment of mental depressions.

The invention relates especially to compounds of the formula I in which X is the oxo radical or hydrogen and the radical $OR_1$, in which $R_1$ is hydrogen, lower alkyl, carboxy-lower alkyl, lower alkoxy-carbonyl-lower alkyl, carbamoyl-lower alkyl, N-lower alkyl-carbamoyl-lower alkyl, N,N-dilower alkyl-carbamoyl-lower alkyl or cyano-lower alkyl and also phenyl or phenyl-lower alkyl or phenoxy-lower alkyl which are unbranched or branched on the $\alpha$-carbon atom, it being possible, in each case, for phenyl to be unsubstituted or substituted by lower alkyl, lower alkoxy, halogen, trifluoromethyl, lower alkoxycarbonyl, carbamoyl, N-lower alkylcarbamoyl, N,N-di-lower alkyl-carbamoyl or cyano, and in which $R_1$ is also acyl and acyl is the group —C(=O)—R, in which R is lower alkyl, lower alkoxy-lower alkyl or halogeno-lower alkyl, and also phenyl or phenyl-lower alkyl, in which phenyl, in each case, can be substituted by lower alkyl, lower alkoxy, halogen and/or trifluoromethyl, $R_2$ is hydrogen, lower alkyl or propargyl, Y is as defined above and Ar is phenyl, naphthyl, tetrahydronaphthyl or anthryl of the indicated type, in which, in each case, phenyl or an aromatic ring of naphthyl or anthryl can be unsubstituted or substituted by lower alkyl, hydroxyl, lower alkoxy, halogen, trifluoromethyl, lower alkoxycarbonyl, carbamoyl, N-lower alkyl-carbamoyl, N,N-di-lower alkyl-carbamoyl, nitro or cyano, it being possible for, in each case, 1, 2 or 3 of the substituents to be present and for these substituents to be either identical or different from one another, and $n_1$, $n_2$ and also $n_1 + n_2$ are as defined above, as well as their acid addition salts, especially pharmaceutically acceptable acid addition salts.

The invention relates in particular to compounds of the formula I in which X is the oxo radical or hydrogen and the radical $OR_1$, in which $R_1$ is hydrogen or lower alkyl having up to 4 carbon atoms, as well as carbamoyl-lower alkyl which is unsubstituted or N-lower alkyl- or N,N-di-lower alkyl-substituted, for example carbamoylmethyl, 1-carbamoyl-2-propyl, 1-N-methylcarbamoyl-2-propyl or 1-N,N-dimethylcarbamoyl-2-propyl, or cyano-lower alkyl, for example cyanomethyl or 1-cyano-2-propyl, and also phenyl-lower alkyl which is preferably branched in the lower alkyl part, for example 1-methyl-2-phenyl-ethyl or 1-methyl-3-phenyl-propyl, carbamoylphenyl-lower alkyl or carbamoylphenoxy-lower alkyl, for example 2-(2- or 4-carbamoylphenyl)-ethyl or 2-(2- or 4-carbamoylphenoxy)-ethyl, or acyl, and acyl is the group —C(=O)—R, in which R is lower alkyl, for example methyl or ethyl, lower alkoxy-lower alkyl or halogeno-lower alkyl having, in each case, up to 4 C atoms in the lower alkyl parts, and also phenyl or phenyl-lower alkyl, it being possible for phenyl to be substituted by lower alkyl or lower alkoxy having, in each case, up to 4 C atoms in the lower alkyl part, halogen and/or trifluoromethyl, and $R_2$ is hydrogen or lower alkyl having up to 4 C atoms, or propargyl, and in which Y is as defined above and Ar is phenyl, naphthyl or tetrahydronaphthyl, it being possible for phenyl, naphthyl or the aromatic ring of tetrahydronaphthyl to be unsubstituted or substituted by lower alkyl, hydroxyl, lower alkoxy, lower alkoxy-carbonyl, N-lower alkyl-carbamoyl or N,N-di-lower alkyl-carbamoyl, lower alkyl having up to 4 C atoms in each case, or substituted by halogen, trifluoromethyl, carbamoyl, nitro or cyano, it being possible for 1 or 2 of these substituents to be present in each case and for the substituents to be either identical or different, and $n_1$, $n_2$ and also $n_1+n_2$ are as defined above, as well as their acid addition salts, especially pharmaceutically acceptable acid addition salts. The invention relates in particular to compounds of the formula I in which X is the oxo radical or hydrogen and the radical $OR_1$, in which $R_1$ is hydrogen, lower alkyl, for example methyl, cyano-lower alkyl, for example cyanomethyl, or carbamoyl-lower alkyl having, in each case, up to 4 C atoms in the lower alkyl part, for example carbamoylmethyl, and also phenyl, which is unsubstituted or substituted in the manner indicated below for Ar, or acyl and acyl is the group —C(=O)—R, in which R is lower alkyl having up to 4 C atoms, for example methyl or ethyl, $R_2$ is hydrogen or lower alkyl having up to 4 C atoms, for example methyl, ethyl or isopropyl, and also propargyl, and Ar is phenyl, naphthyl or 5,6,7,8-tetrahydronaphthyl, which are unsubstituted or at most disubstituted by lower alkyl or lower alkoxy having, in each case, up to 4 C atoms or by halogen, trifluoromethyl, carbamoyl, nitro or cyano, the said substituents being bonded to the aromatic ring and it being possible, in each case, for one, or in the case of lower alkyl, lower alkoxy and halogen, two substituents to be present and for the substituents to be identical or different to one another, and Y, $n_1$, $n_2$ and also $n_1+n_2$ are as defined above, but Y is preferably oxygen and $n_1+n_2$ together are 3, as well as their acid addition salts, especially pharmaceutically acceptable acid addition salts.

The invention relates especially to compounds of the formula I in which X is the oxo radical or hydrogen and the radical $OR_1$, in which $R_1$ is hydrogen or lower alkyl, especially methyl, $R_2$ is hydrogen or lower alkyl, especially methyl, or propargyl and Ar is phenyl, naphthyl or 5,6,7,8-tetrahydronaphthyl, and phenyl can be preferably at most disubstituted by lower alkyl, especially methyl, lower alkoxy, especially methoxy, or halogen, especially chlorine, fluorine or bromine or substituted by trifluoromethyl, it being possible for the said substituents to be identical or different to one another, and Y, $n_1$, $n_2$ and also $n_1+n_2$ are as defined above, but Y is preferably oxygen, $n_1$ and $n_2$ together are 3 and $n_1$ in particular is 1 $n_2$ is 2, as well as their acid addition salts, especially pharmaceutically acceptable acid addition salts.

The invention relates especially to the compounds of the formula I mentioned below:

Trans-3-hydroxy-4-(1-naphthyloxy)-pyrrolidine, trans-3-hydroxy-4-(3,4-dimethyl-phenoxy)-pyrrolidone, trans-3-hydroxy-4-phenylthio-pyrrolidine, trans-3-hydroxy-4-(1-naphthyloxy)-piperidine, trans-3-hydroxy-4-(1-naphthyloxy)-1-methyl-piperidine, trans-3-hydroxy-4-phenylthio-piperidine, trans-3-hydroxy-4-phenylthio-1-methyl-piperidine, trans-3-hydroxy-4-(3,4-dimethyl-phenoxy)-piperidine, trans-3-hydroxy-4-(3,4-dimethyl-phenoxy)-1-methyl-piperidine, trans-4-hydroxy-3-(3,4-dimethyl-phenoxy)-piperidine, trans-4-hydroxy-3-(3,4-dimethyl-phenoxy)-1-methyl-piperidine, trans-3-hydroxy-4-(m-chlorophenoxy)-piperidine, trans-3-methoxy-4-(3,4-dimethyl-phenoxy)-piperidine, trans-3-methoxy-4-(3,4-dimethyl-phenoxy)-1-methyl-piperidine, trans-3-acetyloxy-4-(3,4-dimethyl-phenoxy)-piperidine, trans-3-acetyloxy-4-(3,4-dimethyl-phenoxy)-1-methyl-piperidine, trans-3-hydroxy-4-(3,4-dimethyl-phenoxy)-1-propargyl-piperidine, trans-3-hydroxy-4-(2,3-dimethyl-phenoxy)-piperidine, trans-3-hydroxy-4-(2,3-dimethyl-phenoxy)-1-methyl-piperidine, trans-3-methoxy-4-(2,3-dimethyl-phenoxy)-piperidine, trans-3-methoxy-4-(2,3-dimethyl-phenoxy)-1-methyl-piperidine, trans-3-hydroxy-4-(5,6,7,8-tetrahydro-1-naphthyloxy)-piperidine, trans-3-hydroxy-4-(5,6,7,8-tetrahydro-1-naphthyloxy)-1-methyl-piperidine, trans-3-hydroxy-4-(p-fluoro-phenoxy)-piperidine, trans-3-hydroxy-4-(p-fluoro-phenoxy)-1-methyl-piperidine, trans-3-hydroxy-4-(2-bromo-4-methoxy-phenoxy)-piperidine, trans-3-hydroxy-4-(2-bromo-4-methoxy-phenoxy)-1-methyl-piperidine, trans-3-hydroxy-4-(p-trifluoromethyl-phenoxy)-piperidine, trans-3-hydroxy-4-(p-trifluoromethyl-phenoxy)-1-methyl-piperidine, trans-4-hydroxy-5-(3,4-dimethyl-phenoxy)-hexahydro-1H-azepine, trans-4-hydroxy-5-(3,4-dimethyl-phenoxy)-hexahydro-1-methyl-1H-azepine, trans-4-hydroxy-5-(p-trifluoromethyl-phenoxy)-hexahydro-1-1H-azepine, trans-4-hydroxy-5-(p-trifluoromethyl-phenoxy)-hexahydro-1-methyl-1H-azepine, cis-3-hydroxy-4-(3,4-dimethyl-phenoxy)-piperidine, cis-3-hyroxy-4-(3,4-dimethyl-phenoxy)-1-methyl-piperidine, cis-3-methoxy-4-(3,4-dimethyl-phenoxy)-piperidine, cis-3-methoxy-4-(3,4-dimethyl-phenoxy)-1-methyl-1-piperidine, cis-3-hydroxy-4-(2,3-dimethyl-phenoxy)-piperidine, cis-3-hydroxy-4-(2,3-dimethyl-phenoxy)-1-methyl-piperidine, cis-3-methoxy-4-(2,3-dimethyl-phenoxy)-piperidine, cis-3-methoxy-4-(2,3-dimethyl-phenoxy)-1-methyl-piperidine, cis-3-hydroxy-4-(m-chloro-phenoxy)-piperidine, cis-3-hydroxy-4-(m-chloro-phenoxy)-1-methyl-piperidine, cis-3-hydroxy-4-(1-naphthyloxy)-piperidine, cis-3-hydroxy-4-(1-naphthyloxy)-1-methyl-piperidine, cis-3-hydroxy-4-(5,6,7,8-tetrahydro-1-naphthyloxy)-piperidine, cis-3-hydroxy-4-(5,6,7,8-tetrahydro-1-naphthyloxy)-1-methyl-piperidine, cis-3-hydroxy-4-(p-fluoro-phenoxy)-piperidine, cis-3-hydroxy-4-(p-fluoro-phenoxy)-1-methyl-piperidine, 4-(3,4-dimethyl-phenoxy)-3-piperidone, 4-(2,3-dimethyl-phenoxy)-3-piperidone, 4-(m-chloro-phenoxy)-3-piperidone, 4-(1-naphthyloxy)-3-piperidone, 4-(5,6,7,8-tetrahydro-1-naphthyloxy)-3-piperidone, 4-(p-fluoro-phenoxy)-3-piperidone and 3-(3,4-dimethyl-phenoxy)-4-piperidone and also their acid addition salts, especially pharmaceutically acceptable acid addition salts.

The new compounds of the formula I can be prepared in a manner which is known per se.

Thus, these compounds are obtained, for example, when a compound of the formula

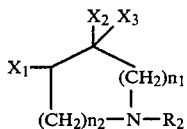

$$\text{(II)}$$

in which $X_1$ and $X_2$ together are epoxy and $X_3$ is hydrogen, or $X_1$ is free or reactive esterified hydroxyl, $X_2$ is the group $-OR_1$ or reactive esterified hydroxyl and $X_3$ is hydrogen, or $X_2$ and $X_3$ together are the oxo radical, and $R_2$ is always as defined under formula I, is reacted with a compound of the formula $$Ar-Y-H \qquad \text{(III)}$$

in which Ar and Y are as defined above, or with a salt thereof. Salts of the starting material of the formula III are, in particular, metal salts, especially alkali metal salts, for example sodium salts or potassium salts.

A reactive esterified hydroxyl group $X_1$ and, where appropriate, $X_2$ is a hydroxyl group esterified by a strong acid, especially a strong inorganic acid, such as a hydrogen halide acid, especially hydrochloric acid, hydrobromic acid or hydriodic acid, or sulphuric acid, or a strong organic sulphonic acid, for example methanesulphonic acid, 4-methylbenzenesulphonic acid or 4-bromobenzenesulphonic acid, and in particular is halogen, for example chlorine, bromine or iodine, or sulphonyloxy with aliphatic or aromatic substituents, for example methylsulphonyloxy or 4-methyl-phenylsulphonyloxy.

The reaction using starting materials in which $X_1$ and, if desired, $X_2$ are reactive esterified hydroxyl, or $X_1$ and $X_2$ together are epoxy, is carried out in a manner which is known per se and is advantageously carried out in the presence of a basic agent, such as of an inorganic base, for example an alkali metal carbonate or hydroxide or alkaline earth metal carbonate or hydroxide, or of an organic base, such as an alkali metal lower alkanolate, and/or of an excess of the basic reactant, usually in the presence of a solvent or solvent mixture and, if necessary, with cooling or warming, for example in a temperature range of about $-20°$ to about $+150°$ and preferably of room temperature to about $100°$, in an open or closed vessel and/or in an inert gas atmosphere, for example in a nitrogen atmosphere.

Suitable inert solvents are, for example, hydrocarbons, such as benzene, ether-like liquids, such as tetrahydrofurane, dioxane or di-lower alkyl ethers of ethylene glycol or of diethylene glycol, for example diethylene glycol dimethyl ether, and also lower alkanones, such as acetone or methyl ethyl ketone, and also carboxylic acid amides, such as N,N-dimethylformamide, and also carboxylic acid nitriles, such as acetonitrile, and also phosphoric acid amides, such as hexamethylphosphoric acid triamide, and also tetramethylurea, sulpholane or lower alkanols such as methoanl, ethanol, n- or iso-propanol or n- or sec.- or tert.-butanol, or mixtures of such solvents. If a compound of the formula III is not employed in the form of a salt, a suitable condensing agent, such as an inorganic or organic base or a mixture thereof, is used in the reaction. Inorganic bases are, for example, the carbonates, hydroxides or oxides or alkali metals or alkaline earth metals and also earth metals, for example lithium carbonate, sodium carbonate, potassium carbonate or calcium carbonate, lithium hydroxide, sodium hydroxide or potassium hydroxide or magnesium oxide or calcium oxide, and also amines, preferably tertiary amines, such as tri-lower alkylamines, for example triethylamine, ethyldiisopropylamine or tris-(2-hydroxy-1-proyl)-amine, 1-lower alkyl-piperidines, for example 1-ethylpiperidine, and also alkali metal alkoholates, such as alkali metal alkanolates, for example sodium methylate or sodium ethylate or sodium tert.-butanolate, potassium methylate or potassium ethylate or potassium tert.-butanolate.

If a compound of the formula II in which $X_1$ is free hydroxyl, $X_2$ is the group $OR_1$ and $X_3$ is hydrogen and $R_2$, $n_1$, $n_2$ and also $n_1+n_2$ are as defined under formula I, but $R_2$ preferably differs from hydrogen, is reacted with a compound of the formula III, such as phenol, p-cresol, m-cresol, 3,4-dimethylphenol, p-methoxyphenol, p-chlorophenol, m-chlorophenol, p-fluorophenol, p-nitrophenol or 2-naphthol, the condensing agent used is triphenylphosphine in the presence of an azodicarboxylate, say a lower alkyl azodicarboxylate, for example diethyl azodicarboxylate. The reaction is carried out in a solvent, say a lower alkanol, such as ethanol, under anhydrous conditions and appropriately under a blanketing gas, say nitrogen, and the reaction temperature is kept in a range of $-20°$ to $+50°$.

The starting materials required for this process variant can be prepared in a manner which is known per se; for example the starting materials of the formula II can be prepared by treating a compound of the formula

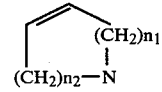

IIa in which $X_8$ is a substituted or unsubstituted aliphatic hydrocarbon radical or a detachable group obtained by reaction with an acyl halide, for example 2,2,2-trichloroethyl chloroformate or benzyl chloroformate, with an oxidising agent, say a peroxide, for example hydrogen peroxide. The reaction is appropriately carried out in a solvent, for example in a solvent of inert character, for example a halogeno hydrocarbon, such as, say, methylene chloride. The reaction is advantageously carried out in the presence of a further agent which promotes the oxidation, for example in the presence of a suitable acid anhydride, such as, say, trifluoroacetic anhydride, and in a temperature range of about $-10°$ to $+50°$. In this case, an epoxide which corresponds to the formula II, and in which $X_1$ and $X_2$ together are epoxy, is obtained and, if desired, this is converted, by reaction with an acid corresponding to the definition of $X_1$, say hydrogen chloride, or a sulphonic acid, such as p-toluenesulphonic acid, or a carboxylic acid, such as an alkanecarboxylic acid, say acetic acid, or an arylcarboxylic acid, such as benzoic acid, if appropriate in a solvent, say dioxane, into a compound of the formula II in which, on the one hand, $X_1$ is an acid radical of the indicated type and $X_2$ is hydroxyl or, on the other hand, $X_1$ is hydroxyl and $X_2$ is the radical $-OR_1$, in which $R_1$ is acyl.

If, corresponding to the definition of $X_8$, an N-acyl derivative of a compound of the formula II is obtained, this derivative is converted by deacylation, say by solvolysis, for example by hydrolysis by means of acid or alkaline compounds, into a compound of the formula II in which $R_2$ is hydrogen. In this case, the starting materials of the formula II can preferentially form in the trans-configuration.

Starting materials of the formula II in which $X_1$ and $X_2$ are hydroxyl can be obtained in a customary manner, for example by oxidising a compound of the formula IIa by means of a permanganate, for example postassium permanganate, in buffered aqueous solution in a suitable temperature range, for example at reduced temperatures, say at $-40°$, and subsequently detaching the radical $X_4$, say by means of hydrolysis in an acid medium. In this case the starting materials can preferentially be obtained in the cis-configuration. If the oxidation is carried out in a known manner using a peroxide in acid solution, say in the presence of a carboxylic acid, say formic acid, in which case the carboxylic acid can appropriately be employed in the form of a per-acid, for example per-formic acid, a starting material of the formula II in which $X_1$ and $X_2$ are hydroxyl can be preferentially obtained in the trans-configuration.

Starting materials of the formula II in which $X_1$ is reactive esterified hydroxyl and $X_2$ is the group $—OR_1$, in which $R_1$ is acyl, are obtained in a customary manner, for example by reacting a compound of the formula II with a carboxylic acid, say a lower alkanecarboxylic acid, such as acetic acid, propionic acid, n-butyric acid, chloroacetic acid or dichloroacetic acid, or an arylcarboxylic acid, say benzoic acid, or a reactive derivative thereof in the presence or the absence of a solvent, say of a hydrocarbon, such as benzene.

Further starting materials of the formula II in which $R_1$ is a substituted or unsubstituted aliphatic or araliphatic hydrocarbon radical can be obtained in a customary manner, for example by reacting a compound of the formula II in which $X_2$ corresponds to the meaning of O-Me and Me is the radical of a metal, say of an alkali metal, such as sodium or potassium, or is an ammonium radical, in a solvent, such as ethanol, n-butanol, benzene or toluene, with a reactive esterified hydroxy compound which is derived from a substituted or unsubstituted aliphatic or araliphatic hydrocarbon.

Further starting materials of the formula II in which $R_1$ is a substituted or unsubstituted aromatic hydrocarbon radical can be obtained by reacting a compound of the formula II in which $X_2$ is hydroxyl with a corresponding aromatic hydroxy compound, say phenol, a substituted phenol or 2-naphthol, in the presence of triphenylphosphine and diethyl azodicarboxylate in an anhydrous solvent, say ethanol, at temperatures of $-20°$ to $+50°$ under a nitrogen atmosphere.

Individual representatives of those starting materials of the formula II, in which $X_1$ is reactive esterified hydroxyl and $X_2$ and $X_3$ together are the oxo radical, are known, such as 1-methyl-3-bromo-4-piperidone [Chemical Abstracts 58, 12544 c], and 3-bromo-4-piperidone and 1-ethyl-3-bromo-4-piperidone [both from Chemical Abstracts 72, 100685 g], and the isomeric compounds 1-methyl-, 1-ethyl- and 1-propyl-4-bromo-3-piperidone can, according to DT-OS 2,205,065, be prepared by bromination of the corresponding known 1-alkyl-3-piperidones [Helv. Chem. Acta 37, 181 (1954)] in glacial acetic acid. Further representatives of both types of compound and also ring homologues can be obtained analogously.

Further starting materials of the formula II, in which $X_2$ is hydroxyl and $X_3$ is hydrogen and $X_1$ is as defined above, and which are in the cis-form or in the trans-form, can be obtained, for example, by means of stereospecific reduction of the compounds of the formula II mentioned further below, in which $X_1$ and $X_3$ together are the oxo radical and $X_1$, $R_{12}$, $n_1$, $n_2$ and also $n_1 + n_2$ are as defined above.

Thus, for example, it is possible, by reduction of an oxo compound of this type by means of Raney nickel in aqueous alkalis, for example 1 N sodium hydroxide solution, over a period of several hours, to obtain a reduction product of the formula II in which the proportion of the cis-isomer is increased or is even predominant, whilst reduction by means of an amalgam, say an alkali metal amalgam, such as 4% strength sodium amalgam, say in aqueous solution, for example over a period of several hours, while cooling with ice and stirring, with subsequent addition of an inorganic base, say of sodium bicarbonate, and further stirring for several hours, gives a reduction product of the formula II, in which the proportion of the trans-isomer is increased or is even predominant.

The use of organometallic hydrides of tin, for example diphenyl tin hydride, in a water-moist ether-like solvent, such as diethyl ether, also opens up the possibility of a reduction which proceeds stereospecifically in the sense described above.

The starting materials of the formula II in which $X_2$ is the group $—OR_1$, which have been described above, can also be in the cis-configuration or trans-configuration and the starting materials used in order to prepare these materials are starting materials of the formula II in which $X_2$ is hydroxyl and which are in the cis-configuration or trans-configuration.

In addition, starting materials of the formula II in which $R_1$ is acyl and which are in the cis-configuration or trans-configuration can be obtained by those esterification methods in which an inversion of the configuration takes place at the same time.

Thus, for example, a compound of the formula II in which $X_2$ is hydroxyl and which is in the trans-configuration can be esterified with a carboxylic acid of the formula R—COOH, for example a lower alkanecarboxylic acid, such as formic acid or acetic acid, or an arylcarboxylic acid, such as benzoic acid, in the presence of triphenylphosphine and diethyl azodicarboxylate in tetrahydrofurane, a compound of the formula II in the cis-configuration being obtained.

The new compounds of the formula I can also be obtained when b), in a compound of the formula IV

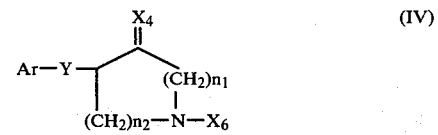

in which Ar, Y, $n_1$, $n_2$ and also $n_1 + n_2$ are as defined above and in which $X_4$ is a free or ketalised oxo radical, or hydrogen and the group $OX_5$, in which $X_5$ has the meaning defined for $R_1$ or is another group which can be replaced by hydrogen, and $X_6$ has the meaning defined for $R_2$ or is a group which can be replaced by hydrogen, with the proviso that at least one of the radicals $X_5$ and $X_6$ is a group which can be replaced by hydrogen, or the oxo radical $X_4$ is in the ketalised form, or in a salt of a compound of the formula IV, the radical or radicals which do not correspond to the definition of the formula I, and also, if desired, an acyl radical $R_1$, are removed and/or, as appropriate, an acyl radical present on the N atom is rearranged onto the O atom.

Salts of starting materials of the formula IV are, in particular, acid addition salts, especially corresponding salts with inorganic acids, for example mineral acids, and also with organic acids.

Detachable radicals $X_5$ and $X_6$ are, especially, acyl groups corresponding to the formula $-C(=O)-R$, in particular lower alkanoyl, for example formyl, acetyl, propionyl or pivaloyl, and also benzoyl or, in particular, acyl radicals of half-derivatives, especially half-esters, of carbonic acid, such as lower alkoxycarbonyl which is unsubstituted or substituted, for example by etherified or esterified hydroxyl, such as aryloxy, for example substituted or unsubstituted phenoxy, halogen, for example chlorine, bromine or iodine, or arylcarbonyl, for example substituted or unsubstituted benzoyl, and is preferably branched in the $\alpha$-position and/or substituted in the $\alpha$-or $\beta$-position, such as lower alkoxycarbonyl, for example methoxycarbonyl or ethoxycarbonyl, especially tert.-lower alkoxy-carbonyl, such as tert.-butoxycarbonyl or tert.-pentyloxy-carbonyl, $\alpha$-aryloxy-lower alkoxycarbonyl, for example bis-(4-methoxyphenoxy)-methoxycarbonyl, or 2-halogeno-lower alkoxy-carbonyl, for example 2,2,2-trichloroethoxycarbonyl, 2-iodoethoxycarbonyl or 2-bromoethoxycarbonyl which can easily be converted into the latter, or $\alpha$-arylcarbonyl-lower alkoxy-carbonyl, for example phenacyloxycarbonyl, or 4-bromophenacyloxycarbonyl, or phenyl- or biphenylyl-lower alkoxy-carbonyl which is unsubstituted or substituted, for example by lower alkoxy, free, etherified or esterified hydroxyl, such as hydroxyl or lower alkoxy, and/or nitro, the aromatic radicals preferably being in the $\alpha$-position and it being possible for one or more substituted or unsubstituted phenyl radicals to be present, such as benzyloxycarbonyl which is unsubstituted or substituted by lower alkyl, for example tert.-butyl, hydroxyl, lower alkoxy, for example methoxy, and/or nitro, for example benzyloxycarbonyl, 4-hydroxy-3,5-di-tert.-butyl-benzyloxycarbonyl, 4-methoxybenzyloxycarbonyl or 4-nitrobenzyloxycarbonyl, diphenylmethoxycarbonyl which is unsubstituted or substituted, for example by lower alkoxy, for example diphenylmethoxycarbonyl or 4,4'-dimethoxydiphenylmethoxycarbonyl, or substituted or unsubstituted biphenylyl-methoxycarbonyl, for example 2-(4-biphenylyl)-2-propoxycarbonyl. The cyano group can also be regarded as a detachable acyl radical $X_5$ and, especially, $X_6$. Further detachable radicals $X_5$ and, in particular, $X_6$ are acyl radicals of organic sulphonic acids, in particular lower alkylsulphonyl, for example methylsulphonyl, or arylsulphonyl, for example phenylsulphonyl or p-tolylsulphonyl.

Further radicals suitable as radicals $X_5$ and $X_6$ which can be replaced by hydrogen are, especially, $\alpha$-aryl-lower alkyl radicals in which aryl in particular is phenyl which is unsubstituted or substituted, for example by lower alkyl, such as tert.-butyl, free, etherified or esterified hydroxyl, such as lower alkoxy, for example methoxy, or halogen, for example chlorine or bromine, and/or nitro, it being possible for one or more aryl radicals to be present, such as unsubstituted or correspondingly substituted benzyl and also trityl.

Other detachable radicals $X_5$ and $X_6$ are, furthermore, easily detachable organic silyl groups and stannyl groups which carry substituted or unsubstituted, especially aliphatic, hydrocarbon radicals as substituents. Silyl or stannyl radicals of this type are, inter alia, tri-lower alkyl-silyl, for example trimethylsilyl or tert.-butyl-dimethyl-silyl, lower alkoxy-lower alkyl-halogeno-silyl, for example chloromethoxy-methyl-silyl, or tri-lower alkyl-stannyl, for example tri-n-butyl-stannyl.

Ketalised oxo radicals $X_4$ are preferably oxo radicals ketalised by methanol, ethanol or ethylene glycol.

Depending on their nature, the groups $X_5$ and $X_6$ which can be replaced by hydrogen can be detached in different ways, preferably by solvolysis or by reduction and especially by hydrogenolysis. Acyl radicals, and also the trityl group, as well as the organic silyl or stannyl radicals can, in general, be removed by solvolysis, in particular by means of hydrolysis and also by means of alcoholysis or acidolysis.

The organic silyl and stannyl radicals can be detached, for example, by treatment with water or an alcohol, such as a lower alkanol, without the addition of a hydrolysis catalyst, such as of an acid or a base.

The acyl radicals of carbonic acid half-derivatives, inter alia including the cyano group, and also of organic carboxylic acids, and also the trityl group, can be detached, and replaced by hydrogen, by means of hydrolysis, usually in the presence of a hydrolysis catalyst, such as a mineral acid, for example hydrochloric acid, hydrobromic acid or sulphuric acid. Suitably substituted benzyloxycarbonyl groups, such as 4-hydroxy-3,5-bis-tert.-butyl-benzyloxycarbonyl, can also be detached, for example, by treatment with a weak base, which can be anhydrous if appropriate, such as an alkali metal salt of an organic carboxylic acid, for example the sodium or potassium salt of 2-ethyl-pentanecarboxylic acid, with an alkali metal salt of a thiophenol, for example the sodium salt of thiophenol, or with a suitable amine, for example ethylamine or cyclohexylamine, and suitably substituted lower alkanoyl, for example trifluoroacetyl, can be detached by hydrolysis under weakly basic conditions. An alkali metal salt of a thiophenol is also suitable for detaching an $\alpha$-arylcarbonyl-lower alkoxycarbonyl group, for example phenacyloxy-carbonyl.

Certain acyl radicals $X_5$ and $X_6$ of half-derivatives, especially half-esters, of carbonic acid can also be detached by means of acidolysis, for example by treatment with a strong organic carboxylic acid, such as formic acid or trifluoroacetic acid, if appropriate in the presence of a suitable nucleophilic compound, such as anisole. These acyl radicals are, especially, tert.-lower alkoxy-carbonyl, for example tert.-butoxy-carbonyl, and also substituted or unsubstituted diphenylmethoxy-carbonyl or biphenylylmethoxy-carbonyl, for example diphenylmethoxycarbonyl or 2(4-biphenylyl)-2-propoxycarbonyl.

The radicals $X_5$ and $X_6$ which can be detached by means of chemical reduction, i.e. by treatment with a suitable metal or a suitable metal compound, are, in particular, 2-halogeno-lower alkoxy-carbonyl or $\alpha$-arylcarbonyl-lower alkoxy-carbonyl, for example 2,2,2-trichloroethoxycarbonyl, 2-iodoethoxycarbonyl or phenacyloxycarbonyl. Suitable reducing agents are, in particular, zinc and zinc alloys, such as zinc/copper, preferably in the presence of a suitable acid, for example acetic acid, which may be diluted with water, and also chromium-II salts, for example chromium-II acetate or chromium-II chloride. Further radicals which can be detached by chemical reduction are the acyl radicals of organic sulphonic acids, for example lower alkyl-sulphonyl, such as methylsulphonyl, or aryl-sulphonyl, such as phenylsulphonyl or p-tolylsulphonyl. Preferably, corresponding starting materials of the formula II in which X₄ is not a free oxo radical are used and the radicals are detached in a conventional manner, for example by means of sodium in a lower alkanol, especially butanol, or preferably by means of a complex hydride, for example by means of sodium bis-(2-methoxyethoxy)-aluminium hydride in benzene.

Radicals which can be detached hydrogenolytically, i.e. on treatment with hydrogen in the presence of a catalyst, are, for example, α-phenyl-lower alkoxy-carbonyl, such as benzyloxycarbonyl, and in particular α-aryl-lower alkyl, such as benzyl. The catalysts used are nickel catalysts and, in particular, noble metal catalysts, such as platinum catalysts or palladium catalysts, and the reaction is carried out under elevated pressure if necessary. Under mild conditions this process variant can also be employed in the case of starting materials of the formula IV containing a free oxo radical X₄.

An acyl radical X₆ which is located on the N atom, corresponds to the definition for R₁ and is to be present as R₁ in the end product can, if desired, as already mentioned, be rearranged onto the O atom, i.e. when the acyl radical on the N atom which does not correspond to the formula I is removed, the hydroxyl group can be acylated by the same radical at the same time. This reaction, which is known as N,O-acyl migration, is carried out in a manner which is known per se, for example by the action of acid reagents, such as of an anhydrous inorganic acid or a derivative thereof, for example hydrogen chloride or thionyl chloride, in an anhydrous medium, for example in anhydrous dioxane or, when hydrogen chloride is used, also in an anhydrous lower alkanol, for example methanol.

The reaction to set free an oxo radical X from a ketalised oxo radical X₄ can likewise be carried out in a conventional manner, for example by acid hydrolysis, for example by means of dilute hydrochloric acid, or by solvolysis, for example by boiling in acetone in the presence of a small amount of benzenesulphonic acid or p-toluenesulphonic acid.

The above reactions are carried out in a manner which is known per se, usually in the presence of a solvent or solvent mixture, it being possible for suitable reactants at the same time also to act as the solvent, and, if necessary, with cooling or with warming, for example in a temperature range of about −20° to about +150°, in an open or closed vessel and/or in the atmosphere of an inert gas, for example nitrogen.

If X₅ is an acyl radical which corresponds to the definition of R₁ and which is intended to remain intact in the desired compound of the formula I, the process conditions for removal of a detachable radical corresponding to the definition of X₆ are so chosen that the acyl group R₁ is not attacked.

The starting materials of the general formula IV can, in turn, be prepared by various processes which are known per se. For example, they can be obtained analogously to the abovementioned process a) by using, in place of the starting material of the formula II, a starting material of the formula

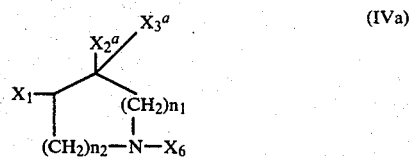

(IVa)

in which n₁, n₂ and also n₁+n₂ are as defined under formula I, X₁ is as defined under formula II, X₆ is as defined under formula IV and X₂ᵃ and X₃ᵃ have the meanings defined under formula II for X₂ and X₃ respectively, or together can also be a ketalised oxo radical.

Furthermore, starting materials of the general formula IV in which X₄ is an oxo radical can also be prepared by oxidation of corresponding compounds in which X₄ is hydrogen and the hydroxyl group. The oxidation can be carried out, for example, by the method of Pfitzner and Moffat, c.f.J. Amer. Chem. Soc. 85, 3027 (1963) and 87, 5661-70 and 5670-78, especially 5676 (1965), by means of dimethylsulphoxide and dicyclohexylcarbodiimide, for example in the presence of pyridine and trifluoroacetic acid, and also by the method of Albright and Goldman, J. Amer. Chem. Soc. 89, 2416 (1967), by means of dimethylsulphoxide and acetic anhydride, by the method of Corey and Kim, J. Amer. Chem. Soc. 95, 7586 (1972), by means of N-chlorosuccinimide and dimethylsulphoxide, or by the method of Oppenauer by reaction with aluminium tri-tert.-butoxide in the presence of an excess of a ketone, such as acetone or cyclohexanone.

Conversely, starting materials of the general formula IV in which X₄ is hydrogen and the hydroxyl group can also be prepared by reduction of corresponding compounds in which X₄ is the oxo radical. Reduction processes which can be used are the conventional processes, for example those mentioned in connection with the preparation of corresponding starting materials of the formula II. The preparation of starting materials of the formula IV in which the hydroxyl group present in X₄ and the radical Ar-Y are in the cis-configuration by stereoselective reduction of oxo compounds which fall under formula IV and, for example, have previously been obtained by oxidation of corresponding trans-hydroxy compounds by the above-mentioned methods is of particular interest.

The reduction can be effected, for example, with hydrogen in the presence of a hydrogenation catalyst, such as, say, Raney nickel, platinum, palladium black or copper chromite, a suitable solvent, say a lower alkanol, for example ethanol or isopropanol, being employed and the hydrogenation being carried out under normal, but especially under elevated, hydrogen pressure. Furthermore, using the method according to Meerwein-Ponndorf-Verley, a metal alkanolate, say an earth metal alkanolate, for example aluminium isopropylate, in the presence of the corresponding alcohol, can be used as the reducing agent, and in this case the alcohol is also employed as the solvent. Alkali metals, for example sodium metal, in a lower alkanol, such as ethanol, or an amalgam, for example sodium amalgam, in water or aqueous lower alkanols are also suitable as reducing agents.

The reduction can, furthermore, be effected by means of Raney nickel in aqueous or aqueous alkaline solution. A stereospecific reduction is possible by means of such process conditions because, in the resulting reduction end product, which is a mixture of the cis- and trans-isomers, the proportion of one or the other isomer is increased or is even predominant.

Thus, for example, it is possible, by reducing a compound of the formula IV by means of Raney nickel in aqueous alkalis, for example 1 N sodium hydroxide solution, preferably over a period of several hours, to obtain a reduction end product in which the proportion of the cis-isomer is increased or is even predominant, whilst reduction by means of an amalgam, say an alkali metal amalgam, such as 4% strength sodium amalgam, say in aqueous solution, for example over a period of several hours while cooling with ice and stirring, with subsequent addition of an inorganic base, say of sodium bicarbonate, and stirring for a further period of several hours, gives a reduction end product in which the proportion of the trans-isomer is increased or is even predominant.

The use of organometallic hydrides of tin, for example diphenyl-tin hydride, in a water-moist ether-like solvent, such as diethyl ether, also opens up a possibility of a reduction which proceeds stereospecifically in the sense described above.

In particular, however, suitable reducing agents are complex hydrides, for example alkali metal borohydrides, such as sodium borohydride, hydroboranes compounds, such as diborane, or alkali metal aluminium hydrides, such as lithium aluminum hydride, and especially alkali metal tri-lower alkylborohydrides and related boron compounds, such as potassium tris-(sec.-butyl)-borohydride and lithium tris-(triamylsilyl)-borohydride, which can be used in an inert solvent of ether-like character, such as dioxane, diethyl ether or, especially, tetrahydrofurane, or if sodium borohydride is used, also in an anhydrous alkanol or a mixture thereof with tetrahydrofurane, or also in aqueous-lower alkanolic solution. Whilst the ratio of the resulting cis-compound to the trans-compound is already about 2 to 1 when the reduction is carried out with potassium borohydride, the corresponding cis-compound is obtained virtually exclusively when the reduction is carried out with potassium tris-(sec.-butyl)-borohydride (K selectride) in tetrahydrofurane in a temperature range of $-78°$ to about $+40°$.

Further starting materials of the formula IV can be obtained when a N-acylpyrroline [in this context see Berichte der deutschen chem. Gesellschaft 22, 2512 (1889) and Chem. Pharm. Bull., 18 (12), 2478 (1970)] or a N-acyl-tetrahydropyridine [J. Pharm. and Pharmacol. 14, 306 (1962)] of the general formula X is oxidised with an oxidising agent, say a peroxide compound, for example with hydrogen peroxide in methylene chloride in the presence of trifluoroacetic anhydride, to give the corresponding 3,4-epoxide compound and the latter is reacted with a compound of the formula III.

The compounds of the formula I in which X is hydrogen and a group $OR_1$, with the exception of the acyloxy groups, and $R_2$ is a substituted or unsubstituted, primary, aliphatic hydrocarbon radical and Ar, Y, $R_1$, $n_1$, $n_2$ and also $n_1+n_2$ are as defined above can also be obtained when (c) the carbonyl group or the alkoxycarbonyl group in a compound of the formula

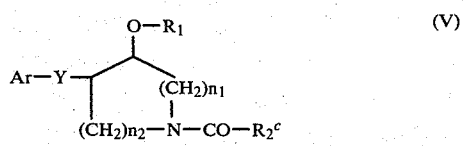

(V)

in which $R_2^c$ is hydrogen, lower alkoxy or a substituted or unsubstituted aliphatic hydrocarbon radical and $R_1$, Ar, Y, $n_1$, $n_2$ and also $n_1+n_2$ are as defined under formula I, is reduced.

Reducing agents which can be used are, for example, metal hydrides, such as diisobutyl-aluminium hydride, or complex metal hydrides, such as lithium aluminium hydride, or borane compounds, especially diborane. The reaction media used are inert solvents, for example those of ether-like character, such as diethyl ether, di-n-butyl ether, tetrahydrofurane or dioxane, and the reaction is carried out in a temperature range of $-20°$ to $+100°$, in an open vessel or, if necessary, in a closed vessel and under a blanketing gas, such as, say, nitrogen. If an acyl group $R_1$ is present, this is replaced by hydrogen during the reduction.

Starting materials of the formula V can be obtained analogously to the methods indicated for the starting materials of the formula IV and some of them are identical to the latter. For example, a compound of the formula Va

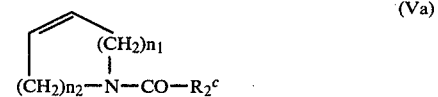

(Va)

can be oxidised with an oxidising agent, say a peroxide compound, for example with hydrogen peroxide, in methylene chloride, in the presence of trifluoroacetic anhydride, to give the corresponding 3,4-epoxide compound and the latter can then be reacted analogously to process (a) with a compound of the formula III.

Furthermore, starting materials of the formula V can also be prepared from end products of the formula I in which hydrogen is present as $R_2$, by means of conventional methods of acylation, it being possible either to ensure, by choice of the acylating agent and its amount and also of the reaction conditions, that a hydroxyl group $OR_1$, which may be present, is not acylated, or, alternatively, to accept the acylation of this group and subsequently to remove the O-acyl group by mild hydrolysis, or, as already mentioned, to detach it in the course of the reduction. The lower alkyl esters, such as the methyl esters and ethyl esters, of the carboxylic acids corresponding to the radical $R_2$ are especially suitable for selective N-acylation but other carboxylic acid derivatives customarily used as acylating agents, such as anhydrides, halides and mixed anhydrides, for example with carbonic acid mono-lower alkyl esters, can also be employed.

Furthermore, starting materials of the formula V can be obtained by isomerisation of compounds of the formula I in which $R_1$ is acyl and $R_2$ is hydrogen. This isomerisation, which is known as O,N-acyl migration, is carried out in a manner which is known per se, for example by the action of alkaline reagents, such as an alkali metal hydroxide, alkali metal carbonate or alkali metal bicarbonate, say sodium hydroxide, potassium carbonate or sodium bicarbonate, or an amine, say ammonia or benzylamine, in a lower alkanol, say methanol, or in water and the reaction is carried out in a temperature range of from about $+10°$ to $+100°$, advantageously while stirring. The isomerisation can also be carried out in an anhydrous solvent, say benzene or toluene, at elevated temperature.

Compounds of the formula I which are obtainable according to the invention can be converted into other compounds of the formula I in a manner which is known per se.

Thus, the novel compounds of the formula I in which X is hydrogen and a hydroxyl group $OR_1$ etherified according to the definition and/or $R_2$ differs from hydrogen, whilst Ar, Y, $n_1$, $n_2$ and also $n_1+n_2$ are as defined under formula I, can be obtained when, in a compound of the formula I in which the hydroxyl group is present as $OR_1$ and/or hydrogen is present as $R_2$, the hydroxyl group is converted into the ether group corresponding to the definition for $R_1$ and/or the hydrogen atom $R_2$ is replaced by a substituted or unsubstituted aliphatic hydrocarbon radical. For example, in order to introduce a radical $R_2$ of this type, a compound of the formula I in which $R_2$ is hydrogen is reacted with a compound of the formula

  (VI)

in which $R_2^d$ is a substituted or unsubstituted aliphatic hydrocarbon radical and $X_7$ is reactive esterified hydroxyl. Possible reactive esterified hydroxyl groups $X_7$ are, for example, the groups mentioned further above for $X_1$.

The reaction according to the invention can be carried out in the presence or absence of an inert organic solvent. Suitable inert solvents are, for example, hydrocarbons, such as benzene, ether-like liquids, such as tetrahydrofurane, or di-lower alkyl ethers of ethylene glycol or of diethylene glycol, for example diethylene glycol dimethyl ether, and also lower alkanones, such as acetone or methyl ethyl ketone, and also carboxylic acid amides, such as N,N-dimethylformamide, and also carboxylic acid nitriles, such as acetonitrile, and also phosphoric acid amides, such as hexamethylphosphoric acid triamide, and also tetramethylurea, sulpholane or lower alkanols such as methanol or ethanol, or mixtures of such solvents. Basic condensing agents, such as inorganic or organic bases or mixtures thereof, are used in the reaction. Inorganic bases are, for example, the carbonates, hydroxides or oxides of alkali metals or alkaline earth metals and also of earth metals, for example calcium carbonate, sodium hydroxide or magnesium oxide or calcium oxide, and also amines, preferably tertiary amines, such as tri-lower alkyl-amines, for example triethylamine, ethyldiisopropylamine or tris-(2-hydroxy-1-propyl)-amine, 1-lower alkyl-piperidines, for example 1-ethylpiperidine, and also alkali metal amides, such as lithium amide, sodium amide or potassium amide, metal alkanolates, such as alkali metal alkanolates, for example sodium methylate or sodium ethylate or sodium tert.-butanolate, potassium methylate or potassium ethylate or potassium tert.-butanolate, and also metal hydrides, such as alkali metal hydrides, alkaline earth metal hydrides or earth metal hydrides, for example sodium hydride, potassium hydride, lithium hydride, calcium hydride or aluminium hydride, and also metal-organic compounds, such as alkyl-lithium or aryl-lithium compounds, for example methyl-, butyl- or phenyl-lithium. When a metal-organic compound of the said type is used, the corresponding N-methyl compound can be formed in situ and in this case one of the said hydrocarbons is appropriately used as the inert solvent. These reactions are carried out in a temperature range of, for example, $-20°$ to $+180°$, if necessary under a blanketing gas, such as, say, nitrogen. Dialkyl sulphates, for example dimethyl sulphate or diethyl sulphate, can also be employed as compounds of the formula VI, and in this case the reaction is carried out, for example, in solutions of aqueous alkalis in a temperature range of about $+10°$ to $+100°$; the reaction can be carried out in non-aqueous media, for example in a lower alkanone or an ether of the indicated type, and in this case it can be advantageous to employ a condensing agent of the indicated type, for example an alkali metal carbonate, such as potassium carbonate, or a metal-organic compound, such as, say, methyl-lithium; in this case the reaction is preferably carried out in a temperature range of about $+10°$ to $+90°$.

In place of a compound of the formula VI, it is also possible to employ an oxo compound of the formula $R_4$—C(=O)—$R_5$ (VIa), in which $R_4$—C(=)—$R_5$ is the divalent radical corresponding to the monovalent radical $R_2^d$, under reducing conditions in order to replace a hydrogen atom $R_2$ by an aliphatic hydrocarbon radical.

The reducing agent used is, for example, formic acid, or hydrogen in the presence of a hydrogenation catalyst, for example Ranet nickel, platinum oxide or palladium-on-charcoal, and also a complex metal hydride, such as, for example, lithium aluminium hydride, sodium dihydro-[bis-(2-methoxy-ethoxy)]aluminate or tri-tert.-butoxy-aluminium hydride or sodium borohydride. This reductive alkylation is carried out in a suitable solvent, such as a lower alkanol, for example methanol or ethanol, or an ether, such as tetrahydrofurane or diethyl ether. If formic acid is used as the reducing agent, this can at the same time serve as the solvent. These reactions are preferably carried out in a temperature range of $+10°$ to $+100°$.

In order to convert the hydroxyl group $OR_1$ into an ether group which corresponds to the definition of $R_1$ in formula I, a compound of the formula I in which $R_1$ is hydrogen and $R_2$ is a substituted or unsubstituted aliphatic hydrocarbon radical is reacted with a compound of the formula $R_6$—$X_1$ (VII), in which $R_6$ is a substituted or unsubstituted aliphatic, araliphatic or aromatic hydrocarbon radical and $X_1$ is as defined above. The reaction with compounds of the formula VII in which $X_1$ is reactive esterified hydroxyl and $R_6$ is not an aromatic hydrocarbon radical is advantageously carried out in a solvent, for example of the type indicated above, with the exception of water, in the presence of a basic condensing agent. The condensing agent used is, for example, one of those mentioned above; however, a preferred condensing agent is a metal alkanolate, for example of the indicated type, in particular sodium methylate or sodium ethylate, or potassium methylate or potassium ethylate, and especially sodium tert.-butanolate and potassium tert.-butanolate, and also a metal hydride, especially lithium hydride, or a metal-organic compound, especially methyl-lithium or phenyl-lithium. With this reaction it can be advantageous first to convert the hydroxyl group $OR_1$ in situ into the corresponding metal compound and then to react the latter with the compound of the formula VII, the reaction being carried out in an open or closed vessel and, if necessary, under a blanketing gas, say nitrogen.

If a compound of the formula VII in which $X_1$ is hydroxyl is employed in order to etherify the hydroxyl group $OR_1$, the reaction is carried out in a solvent, said a halogenated hydrocarbon, such as, say, methylene chloride, or an ether, say diethyl ether, in the presence of an anhydrous substance having a strongly acid reaction, such as, say, hydrogen chloride, boron fluoride or its adducts with ethers, or strong anhydrous acids, for example anhydrous phosphoric acid or fluoroboric acid, or a Lewis acid, such as, say, antimony pentafluoride or tin tetrachloride, preferably in a temperature range of $-20°$ to $+50°$, in an open vessel, but especially in a closed vessel. It is also possible to use mixtures of the substances having an acid reaction which have been mentioned above, and further acids, for example concentrated sulphuric acid and/or trifluoroacetic acid, can be added.

If the reaction is carried out with a compound of the formula VII in which $R_6$ is a substituted or unsubstituted aromatic hydrocarbon radical and $X_1$ is hydroxyl, such as, say, phenol, p-cresol, m-cresol, p-methoxyphenol, p-chlorophenol, p-nitrophenol or 2-naphthol, the condensing agent used is triphenylphosphine in the presence of an azodicarboxylate, say a lower alkyl azodicarboxylate, for example diethyl azodicarboxylate. The reaction is carried out in a solvent, say a lower alkanol, such as ethanol, under anhydrous conditions and appropriately under a blanketing gas, say nitrogen, and the reaction temperature is kept in a range of $-20°$ to $+50°$.

The compounds of the general formula VII in which $R_6$ is a substituted or unsubstituted aromatic hydrocarbon radical and $X_1$ is a reactive esterified hydroxyl group, especially halogen, which can be used are only those which contain at least one activating substituent bonded to an aromatic nucleus, for example 1-chloro-2-nitrobenzene, 1-chloro-4-nitrobenzene, 1-chloro-2,4-dinitrobenzene or, especially, 1-chloro-3-fluorobenzene. These compounds can be reacted, for example, with alkali metal compounds, for example sodium compounds or lithium compounds, of compounds of the general formula I, in which $OR_1$ is a hydroxyl group, in an inert organic solvent, for example those mentioned further above, especially in N,N-dimethylformamide, at room temperature or moderately elevated temperatures, for example at about 50°–70°.

The reactions described above, which proceed with participation of the cyclic NH group and/or the hydroxyl group $OR_1$, can also be carried out at the same time if the same radicals are introduced into both groupings.

The novel compounds of the formula I in which X is hydrogen and an acyloxy group $OR_1$ according to the definition and $R_2$ is a substituted or unsubstituted aliphatic hydrocarbon radical and Ar, Y, $n_1$, $n_2$ and also $n_1+n_2$ are as defined under formula I can also be obtained when, (e) a compound of the formula I in which the hydroxyl group is present as $OR_1$ and a substituted or unsubstituted aliphatic hydrocarbon radical is present as $R_2$ and Ar, Y, $n_1$, $n_2$ and also $n_1+n_2$ are as defined under formula I is reacted with a carboxylic acid of the formula

R—CO—OH    (VIII)

in which R is a substituted or unsubstituted aliphatic, cycloaliphatic, aromatic or araliphatic hydrocarbon radical, or with a reactive derivative thereof.

The reaction with a free acid of the formula VIII can be carried out, for example, by heating the reactants, with removal of the water formed, such as with the formation of azeotropic water/solvent mixtures. Suitable solvents are, for example, butanol, benzene or xylene and the reaction can be carried out in the presence of further acid substances, preferably esterifying acid substances, for example concentrated sulphuric acid, thionyl chloride, benzenesulphonic acid, p-toluenesulphonic acid, chlorosulphonic acid, phosphoric acid or perchloric acid.

Furthermore, the acylation with a carboxylic acid of the formula VIII can be carried out in the presence of a condensing agent, such as a carbodiimide, for example N,N'-dicyclohexyl-carbodiimide, or a suitable carbonyl compound, such as carbonyldiimidazole, and such reactions are carried out in an inert anhydrous reaction medium.

Preferably, however, a compound of the formula I having the definition given above is reacted with a reactive derivative of an acid of the formula VIII. Such a derivative is, especially, an anhydride, say a mixed or inner anhydride, of such an acid, and also a reactive ester, as well as an organic silyl or stannyl ester, or a reactive amide of such an acid.

A mixed anhydride is, for example, an anhydride which is formed with a derivative, for example an ester, of a halogenoformic acid, for example of chloroformic acid, such as a lower alkyl chloroformate, for example isobutyl chloroformate, and also with a hydrogen halide acid, for example hydrochloric acid or hydrobromic acid, and also with hydrazoic acid; anhydrides with the latter are the corresponding acid halides, for example acid chlorides or acid bromides, and acid azides. Inner anhydrides are, for example, the ketenes corresponding to the acid of the formula VIII or the lactones corresponding to suitable hydroxycarboxylic acids.

Reactive esters of carboxylic acids of the formula VIII are, for example, esters with lower alkanols which, in the α-position, contain an electron-withdrawing group, such as a cyano group, for example with cyanomethanol, with phenols or phenyl-lower alkanols, such as benzyl alcohols, which are unsubstituted or substituted, for example by nitro or halogen, such as chlorine, for example phenol, 4-nitrophenol, 2,3,4,5,6-pentachlorophenol or 4-nitrobenzyl alcohol, or with suitable N-hydroxy-carboxylic acid amides or acid imides, for example N-hydroxy-succinimide or N-hydroxyphthalimide. Suitable silyl and stannyl esters are, in particular, silyl or stannyl esters trisubstituted by aliphatic groups, such as tri-lower alkyl-silyl or -stannyl esters, for example the trimethylsilyl esters or tri-n-butyl-stannyl esters.

Reactive amides of acids of the formula VIII are, for example, the corresponding N-acyl compounds of aza-heterocyclic compounds, such as 1-acyl-imidazolides or 3-acyl-hydantoins which are unsubstituted or substituted in the 1-position and/or 5-position, for example by lower alkyl, for example 3-acyl-1,5,5-trimethyl-hydantoin, and also the corresponding N,N-di-acyl-amides of carboxylic acids, especially for lower alkanecarboxylic acids, for example formic acid or acetic acid.

The abovementioned reactive derivatives of a carboxylic acid of the formula VIII can be employed as such or can be formed under the conditions of the reaction, for example from the free carboxylic acid or another derivative thereof in the presence of a suitable reagent which effects formation of the reactive derivative, for example of an anhydride or of a reactive ester or amide.

The reaction of compounds, according to the definition, of the formula I with carboxylic acids of the formula VIII, or derivatives thereof, is carried out in a manner which is known per se, usually in the presence of a solvent, it being possible for a suitable esterifying agent at the same time to serve as the solvent, and if necessary, in the presence of, for example, acid binding agents and/or catalysts, with cooling or warming, for example in a temperature range of about $-20°$ to about $150°$, in a closed vessel and/or in an inert gas atmosphere, for example a nitrogen atmosphere.

The reaction with symmetrical or mixed anhydrides, such as acid halides, can be carried out in the presence of agents which influence the acylation, the agents used being, for example, acid-binding agents, such as inorganic and also organic bases, and also mixtures thereof, or acid agents (for example when acid halides, for example acid chlorides, are used), such as organic acids, which at the same time can also serve as the solvent. Inorganic bases are, for example, the carbonates, hydroxides or oxides of alkali metals or alkaline earth metals, and also earth metals, for example calcium carbonate, sodium hydroxide or magnesium metal, and also amines, preferably tertiary amines, such as tri-lower alkyl amines, for example triethylamine, ethyl-diisopropylamine or tris-(2-hydroxy-1-propyl)-amine, 1-lower alkyl-piperidines, for example 1-ethylpiperidine, or bases of the pyridine type, for example pyridine or picoline, or 4-dimethylamino-quinoline, and also mixtures thereof. Suitable organic acids are, for example, strong organic carboxylic acids, such as strong, substituted or unsubstituted carboxylic acids, for example trifluoroacetic acid.

In order to increase the rate of reaction and/or to lower the reaction temperatures, it can be advantageous to add to the reaction mixture further substances, preferably substances having a catalytic action and in particular acid substances, such as inorganic acids or derivatives thereof, for example hydrogen chloride, sulphuric acid, phosphoric acid, thionyl chloride, perchloric acid, phosphorus oxychloride or phosphorus pentachloride, and also strong organic sulphonic acids and carboxylic acids, for example methanesulphonic acid, benzenesulphonic acid, p-toluenesulphonic acid, 4-chlorosulphonic acid or 3-nitrobenzenesulphonic acid or trifluoroacetic acid, as well as the acids of the formula VIII corresponding to the anhydrides, and also Lewis acids, for example antimony pentafluoride and also boron trifluoride or its adducts with ethers. Moreover, the addition of carboxylic acid salts corresponding to an acid of the formula VIII, such as of alkali metal salts, alkaline earth metal salts or earth metal salts, and also of corresponding heavy metal salts, for example zinc salts, tin salts, antimony salts or lead salts, as well as of unsubstituted or N-substituted ammonium salts of acids of the formula VIII can have a favourable influence on the acylation.

Ketenes, as inner anhydrides, can customarily be used without additional reagents but, furthermore, can also be used in the presence of an acid condensing agent and in the presence of a suitable solvent.

The acylation with the aid of reactive amines of acids of the formula VIII is appropriately carried out in the presence of a condensing agent, such as of a basic agent, for example of an anhydrous alkali metal carbonate, hydroxide or oxide or alkaline earth metal carbonate, hydroxide or oxide, or especially of an alkali metal amide or lower alkanolate, alkaline earth metal amide or lower alkanolate or earth metal amide or lower alkanolate, for example sodium amide or potassium amide or lithium methanolate, ethanolate or, especially, tert.-butanolate, sodium methanolate, ethanolate or, in particular, tert.-butanolate or aluminium methanolate, ethanolate or, in particular, tert.-butanolate.

Reactive esters, as acylating agents, can be used in the presence of basic reagents, for example those mentioned above, and also in the presence of acid condensing agents. The latter are, inter alia, organic sulphonic acids, for example p-toluenesulphonic acid, and also mineral acids, for example phosphoric acid or an acid which is derived therefrom and is obtainable by partial hydrolysis of phosphorus oxychloride with water.

Acyl compounds of the formula I in which $R_1$ is acyl and which are in the cis-configuration or the trans-configuration can also be obtained by means of those esterification methods which are associated with an inversion of configuration. Thus, for example, an acyl compound of the formula I in the cis-configuration can be obtained from a compound, according to the definition, of the formula I in the trans-configuration by esterification with a lower alkanoic acid, such as formic acid, acetic acid or propionic acid, or an arylcarboxylic acid, such as benzoic acid, in the presence of triphenylphosphine and an azodicarboxylate, say diethyl azodicarboxylate, in an inert solvent, say tetrahydrofurane. In this case the reaction is carried out in a temperature range of $-20°$ to $+60°$ and preferably of $-10°$ to $+30°$, if appropriate under a blanketing gas, say nitrogen.

The corresponding compounds of the formula I can be prepared by reacting a corresponding compound of the formula II, which in each case can also be in the cis-configuration or trans-configuration, with a compound of the formula III, as described above.

The novel compounds of the formula I in which X is the oxo radical and $R_2$, Ar, Y, $n_1$, $n_2$ and also $n_1+n_2$ are as defined under formula I, but $R_2$ preferably differs from hydrogen, can also be prepared when, (f) a corresponding compound of the formula I in which X is hydrogen and the hydroxyl group and $R_2$, Ar, Y, $n_1$, $n_2$ and also $n_1+n_2$ are as defined under formula I, but $R_2$ preferably differs from hydrogen, is oxidised. The oxidation can be carried out, for example, by the methods mentioned for the preparation of starting materials of the formula IV, and especially by the Oppenauer method.

Conversely, the novel compounds of the formula I in which X is hydrogen and, as the radical $OR_1$, the hydroxyl group, and $R_2$, Ar, Y, $n_1$, $n_2$ and also $n_1+n_2$ are as defined under formula I can also be prepared when, (g) a corresponding compound of the formula I in which X is the oxo radical is reduced. The methods which can be used for the reduction are, again, the methods mentioned for the preparation of corresponding starting materials of the formula IV. The reaction sequence comprising the oxidation and the subsequent stereospecific reduction, for example by the methods indicated above, provides a possibility in the case of the end products of the formula I also, as in the case of the starting materials of the formula IV, for converting trans-hydroxy compounds of the formula I in good yield into cis-hydroxy compounds of the formula I.

Furthermore, substituents present in resulting compounds of the formula I can be converted into other substituents according to the definition.

Thus, for example, unsaturated substituents, such as lower alkenyl, in resulting compounds can be reduced, for example by treatment with catalytically activated hydrogen.

A free carboxyl group can be esterified or amidated in a conventional manner, for example by treatment with an alcohol in the presence of an acid or with a diazo compound or, respectively, by reaction with ammonia or with a primary or secondary amine, if necessary in the presence of a water-binding agent, such as dicyclohexylcarbodiimide, or by converting the carboxyl group into a halogenocarbonyl group, for example a chlorocarbonyl group, and treating this with an alcohol or a corresponding metal compound, for example an alkali metal compound, or, respectively, reacting it with ammonia or with a primary or secondary amine.

In compounds having an esterified carboxyl group, the latter can, in a conventional manner, be converted into the free carboxyl group, for example by hydrolysis, preferably in the presence of a suitable base or acid, for example of a strong mineral acid, or converted into the corresponding carbamoyl group, for example by ammonolysis or aminolysis.

Compounds containing a carbamoyl group can be dehydrated to the corresponding cyano compounds in a conventional manner, for example by the action of dehydrating agents, such as phosphorus pentoxide or phosphorus oxychloride, preferably at higher temperatures.

Compounds containing a cyano group can, in a conventional manner, be saponified to the corresponding carbamoyl compounds or directly to the carboxyl compounds, for example in the presence of a concentrated mineral acid, or alcoholised to the corresponding compounds containing an esterified carboxyl group, for example by the addition of alcohols in the presence of an anhydrous acid, such as hydrogen chloride, and subsequent hydrolysis of the imido-ester formed.

As in the case of the processes of preparation, care must also be taken when carrying out the additional steps that undesired side reactions which could result in the conversion of the groupings present, especially in an acyl group $R_1$ being detached, are avoided. The reactions described above can, as desired, be carried out at the same time or consecutively and can also be carried out in any desired sequence. If necessary they are carried out in the presence of diluents, condensing agents and/or agents having a catalytic action, at reduced or elevated temperature, in a closed vessel under pressure and/or in an inert gas atmosphere.

Depending on the process conditions and the starting materials, the novel compounds are obtained in the free form or in the form of their salts, which the invention also comprises, and the novel compounds or salts thereof can also be in the form of hemihydrates, monohydrates, sesquihydrates or polyhydrates. Acid addition salts of the novel compounds can be converted in a manner which is known per se, for example by treatment with basic agents, such as alkali metal hydroxides, alkali metal carbonates or alkali metal bicarbonates or ion exchangers, into the free compounds and these, in turn, if they contain acid substituents, such as phenolic hydroxyl groups or carboxyl groups, can be converted by means of suitable strong basic substances into salts with bases. On the other hand, resulting free bases can form acid addition salts with organic or inorganic acids, for example with the abovementioned acids. The acids and bases used to prepare acid addition salts and salts with bases are, in particular, those which are suitable for the formation of pharmaceutically acceptable salts.

These or other salts, especially acid addition salts of the novel compounds, for example picrates or perchlorates, can also be used for purification of the resulting free bases by converting the free bases into salts, separating off and purifying these salts and again setting the bases free from the salts.

Depending on the choice of the starting materials and the procedures, the novel compounds can be in the form of optical antipodes or racemates or, if they contain at least two asymmetrical carbon atoms, can also be in the form of mixtures of racemates.

Resulting mixtures of racemates can be separated, on the basis of the physico-chemical differences between the diastereomers, into the two stereoisomeric (diastereomeric) racemates in a known manner, for example by chromatography and/or fractional crystallisation.

Resulting racemates can be resolved into the antipodes by methods which are known per se, for example by recrystallisation from an optically active solvent, by treatment with suitable microorganisms or by reaction with an optically active substance, especially an acid, which forms salts with the racemic compound and separation of the mixture of salts obtained in this way, for example on the basis of the different solubilities, into the diastereomeric salts, from which the free antipodes can be set free by the action of suitable agents. Examples of optically active acids which are particularly commonly used are the D and L forms of tartaric acid, di-o-tolyl tartaric acid, malic acid, mandelic acid, camphorsulphonic acid, glutamic acid, aspartic acid or quinic acid. Advantageously, the more active of the two antipodes is isolated.

Depending on the process conditions and the starting materials, the end products of the formula I are obtained in the form of pure isomers or in the form of mixtures of isomers. Such mixtures can be, for example, mixtures of compounds in the cis-configuration and trans-configuration.

Mixtures of isomers of the above type are separated into the pure isomers in a conventional manner, for example by means of crystallisation and/or chromatographic methods, say by means of a silica gel column using conventional solvent mixtures as the eluants. Resulting cis-isomers can be converted into trans-isomers in a conventional manner, for example by treatment of a solution of a cis-isomer, say in acetic acid or methanol, in the presence of catalytic amounts of heavy metal salts, say mercury acetate, or by treatment of a solution of the cis-isomer is a hydrocarbon, say benzene, with azo compounds, say azodiisobutyronitrile and subsequent treatment with a solution of iodine in a solvent, for example a hydrocarbon, such as benzene or nitrobenzene. Furthermore, the conversion can be effected by treatment of a solution of the cis-compound in an acid, say acetic acid, which contains small amounts of a strong acid, say perchloric acid.

Resulting trans-isomers can be converted into the cis-isomers in a conventional manner, say by irradiating a solution of the trans-isomers in a hydrocarbon, such as benzene, which can contain an activator, say diphenyl sulphide, by means of short-wave light, say the light from a mercury vapour high pressure lamp. Furthermore, a compound of the formula I which is in the trans-configuration and in which $R_1$ is as defined above, for example is acyl, can be converted into the corresponding compound in the cis-configuration by the action of a lower alkanol, say ethanol, in the presence of an alkali metal salt, for example potassium acetate, or of an alkaline earth metal salt, for example calcium carbonate.

The invention also relates to those embodiments of the process in which a compound obtainable as an intermediate at any stage of the process is used as the starting material and the missing process steps are carried out, or the process is discontinued at any stage, or in which a starting material is formed under the reaction conditions, or in which a reactant may be present in the form of its derivatives, such as salts.

The starting materials used for carrying out the reactions according to the invention are appropriately those which lead to the groups of end products mentioned in particular initially and especially to the end products specifically described or singled out, for example starting materials can be in the cis-configuration or the trans-configuration.

The new compounds can be used, for example, in the form of pharmaceutical compositions which are suitable for enteral, for example oral or rectal, or parenteral administration and contain a therapeutically effective amount of the active compound, if desired together with pharmaceutically acceptable excipients, which excipients can be inorganic or organic, and solid or liquid. Thus, tablets or gelatine capsules are used which contain the active compound, i.e. a compound of the formula I or a pharmaceutically acceptable salt thereof, together with diluents, for example lactose, dextrose, sucrose, mannitol, sorbitol, cellulose and/or glycine, and/or lubricants, for example silica, talc or stearic acid or salts thereof, such as magnesium stearate or calcium stearate, and/or polyethylene glycol. Tablets can also contain binders, for example magnesium aluminium silicate, starches, such as maize starch, wheat starch, rice starch or arrowroot, gelatine, tragacanth, methylcellulose, sodium carboxymethylcellulose and/or polyvinylpyrrolidone, and, if desired, disintegrating agents, for example starches, agar or alginic acid or a salt thereof, such as sodium alginate, and/or effervescent mixtures, or adsorbents, dyestuffs, flavourings and sweeteners. Furthermore, the new pharmacologically active compounds can be used in the form of compositions which can be administered parenterally or in the form of infusion solutions. Such solutions are preferably isotonic aqueous solutions or suspensions and, for example in the case of lyophilised formulations which contain the active compound on its own or together with an excipient, for example mannitol, these can be prepared prior to use. The pharmaceutical compositions can be sterilised and/or contain auxiliaries, for example preservatives, stabilisers, wetting agents and/or emulsifiers, solubilising agents, salts for regulating the osmotic pressure and/or buffers. The present pharmaceutical compositions, which, if desired, can contain further pharmacologically active substances, are prepared in a manner which is known per se, for example by means of conventional mixing, granulating, dragee-making, dissolving or lyophilising processes, and contain from about 0.1% to 100% and especially from about 1% to about 50% of the active compound and lyopholisates contain up to 100% of the active compound.

The dosage can depend on various factors, such as the mode of application, the species the age and/or the state of health of the individual. The doses to be administered per day are, for oral administration, between about 0.5 mg/kg and about 50 mg/kg, and for warm-blooded animals weighing about 70 kg in particular are between 0.05 and about 3.0 g.

The examples which follow serve to illustrate the invention; temperatures are given in degrees centigrade.

EXAMPLE 1

4.5 g (0.015 mol) of 3-hydroxy-4-chloro-1-($\beta,\beta,\beta$-trichloroethoxycarbonyl)-pyrrolidine are dissolved in 45 ml of 90% strength acetic acid and the solution is treated, while cooling with an ice/water bath, with 4.5 g of zinc dust in portions. The mixture is stirred for one hour at room temperature and then filtered by means of a filter aid based on diatomaceous earth and the filtrate is evaporated to dryness under a high vacuum, crude 3-hydroxy-4-chloro-pyrrolidine being obtained as a white residue.

The resulting crude product is taken up in 200 ml of acetonitrile and the solution is heated together with 2.85 g (0.03 mol) of phenol and 60 ml of 2 N sodium hydroxide solution for 15 hours under reflux. After cooling, the reaction mixture is concentrated to about half its volume under a water pump vacuum and is then diluted with water and extracted by shaking with b 3 times 100 ml of methylene chloride. The organic phase is washed 3 times with 1 N sodium hydroxide solution and 3 times with aqueous sodium chloride solution, dried over sodium sulphate and evaporated under a water pump vacuum. The oily residue is dissolved in a little chloroform and purified on a small silica gel column. Trans-3-hydroxy-4-phenoxy-pyrrolidine is isolated by elution with a chloroform/methanol mixture (1:1) and with a solution of fumaric acid in methanol/ether this gives a neutral fumarate with a melting point of 145°–146°.

3-Hydroxy-4-chloro-1-[$\beta,\beta,\beta$-trichloroethoxycarbonyl]-pyrrolidine, which is used as the starting material, can be prepared as follows:

(a) 40.0 g (0.25 mol) of N-benzyl-3-pyrroline are dissolved in 400 ml of benzene. 53.0 g (0.25 mol) of 2,2,2-trichloroethyl chloroformate are introduced into this solution in the course of 30 minutes, at 0° and under a nitrogen atmosphere. The reaction mixture is stirred for a further 1 hour at 0°, then washed at room temperature twice with, in each case, 100 ml of a mixture of water and 2 N hydrochloric acid (3:1) and then twice with water, dried over sodium sulphate and evaporated under a water pump vacuum. The oily residue is distilled under a high vacuum and, after 24 g of benzyl chloride has been separated off, N-($\beta,\beta,\beta$-trichloroethoxycarbonyl)-3-pyrroline with a boiling point of 84°–85° C./0.12 mm Hg is obtained.

(b) 12 ml of 90% strength hydrogen peroxide (0.48 mol) are dissolved in 40 ml of methylene chloride and the solution is treated at 0° with 63.5 ml (0.45 mol) of trifluoroacetic anhydride. After stirring for 15 minutes at 0°, the solution is added dropwise to a suspension, which is kept at 0°, of 196 g of anhydrous disodium hydrogen phosphate in 800 ml of methylene chloride, in which 41.8 g (0.17 mol) of N-($\beta,\beta,\beta$-trichloroethoxycarbonyl)-3-pyrroline has been dissolved. Subsequently, the reaction mixture is stirred for 2 hours at room temperature and then stirred into 900 ml of water and the resulting mixture is stirred for a further one hour. The organic phase is separated off and the aqueous phase is extracted by shaking with 3 times 200 ml of methylene chloride; the combined organic phases are washed successively with aqueous sodium chloride solution, aqueous iron-II sulphate solution and then with water, dried over sodium sulphate and evaporated under a water pump vacuum, whereupon 3,4-epoxy-1-($\beta,\beta,\beta$-trichloroethoxycarbonyl)-pyrrolidine is obtained in the form of white crystals with a melting point of 52°–55°.

(c) 4.0 g of 3,4-epoxy-1-($\beta,\beta,\beta$-trichloroethoxycarbonyl)-pyrrolidine are dissolved in 15 ml of dioxane, and the solution is treated with 50 ml of 6 N hydrochloric acid. The slightly exothermic reaction is kept at room temperature by means of a water bath, and the reaction mixture is stirred for 15 hours, then diluted with water and extracted 3 times with 100 ml of methylene chloride. The organic phase is washed with 0.1 N sodium hydroxide solution and then with aqueous sodium chloride solution, dried over sodium sulphate and then evaporated to dryness, first under a water pump vacuum and then under a high vacuum, 3-hydroxy-4-chloro-1-($\beta,\beta,\beta$-trichloroethoxycarbonyl)-pyrrolidine being obtained as a slightly yellow oil.

EXAMPLE 2

2.6 g (0.01 mol) of the 3,4-epoxy-1-($\beta,\beta,\beta$-trichloroethoxycarbonyl)-pyrrolidine described in Example 1 are heated together with 1.88 g (0.02 mol) of phenol and 10 ml of 1 N sodium hydroxide solution in 30 ml of acetonitrile for 5 hours under reflux. After cooling, the reaction mixture is diluted with water and extracted 3 times with methylene chloride, and the organic phase is washed twice with 2 N sodium hydroxide solution and then once with water, dried over sodium sulphate and evaporated under a water pump vacuum. The resulting oil crystallises from methylene chloride/hexane and gives trans-3-hydroxy-4-phenoxy-1-($\beta,\beta,\beta$-trichloroethoxycarbonyl)-pyrrolidine with a melting point of 100°–103°.

1.77 g (0.005 mol) of the resulting trans-3-hydroxy-4-phenoxy-1-($\beta,\beta,\beta$-trichloroethoxycarbonyl)-pyrrolidine are dissolved in 20 ml of 90% strength acetic acid and the solution is treated at 0° with 2 g of zinc dust in portions. The reaction mixture is then stirred at room temperature for one hour and filtered through a layer of diatomaceous earth and the filtrate is rendered alkaline with concentrated sodium hydroxide solution and extracted 3 times with ether. The organic phase is washed with water, dried over calcium chloride and evaporated under a water pump vacuum, and trans-3-hydroxy-4-phenoxy-pyrrolidine is obtained in the form of the crude base, which crystallises from methylene chloride/hexane; melting point 120°–122°. The neutral fumarate of this compound, which has a melting point of 144°–146°, is obtained by reaction with a solution of fumaric acid in methanol/ether.

EXAMPLE 3

21.9 g (0.1 mol) of 3,4-epoxy-1-carbobenzyloxy-pyrrolidine [S. Oida et al., Chem. Pharm. Bull., 18 (12), 2478 (1970)] are dissolved, together with 18.8 g (0.2 mol) of phenol and 100 ml of 2 N sodium hydroxide solution (0.2 mol) in 300 ml of acetonitrile. The reaction mixture is heated under reflux for 5 hours and after cooling is diluted with 600 ml of water and extracted by shaking with methylene chloride. The organic phase is washed with 2 N sodium hydroxide solution and then with water, dried over sodium sulphate and evaporated under a water pump vacuum and trans-3-hydroxy-4-phenoxy-1-carbobenzyloxy-pyrrolidine is obtained in the form of a pale yellow oil.

28.2 g (0.09 mol) of trans-3-hydroxy-4-phenoxy-1-carbobenzyloxy-pyrrolidine are dissolved in 280 ml of ethanol and hydrogenated in the presence of 3 g of a 5% strength palladium-on-charcoal catalyst under normal pressure and at room temperature. After the absorption of hydrogen has ceased, the catalyst is filtered off by means of diatomaceous earth and the filtrate is evaporated under a water pump vacuum. The residue is crystallised from methanol/ether and gives trans-3-hydroxy-4-phenoxy-pyrrolidine with a melting point of 120°–122°. The crystalline neutral fumarate with a melting point of 145°–146° is obtained by reacting the base with a solution of fumaric acid in methanol/ether.

EXAMPLE 4

Analogously to the procedure described in Example 3, crystalline trans-3-hydroxy-4-(p-carbamoyl-phenoxy)-1-carbobenzyloxy-pyrrolidine with a melting point of 190°–192° is obtained from 5.0 g (0.023 mol) of 3,4-epoxy-1-carbobenzyloxy-pyrrolidine and 6.25 g (0.046 mol) of 4-hydroxy-benzamide, after recrystallisation of the product from methylene chloride/methanol. After the hydrogenation, which is carried out analogously to Example 3, of 0.07 mol of this compound, trans-3-hydroxy-4-(p-carbamoyl-phenoxy)-pyrrolidine is obtained in the form of white crystals with a melting point of 182°–184°, after recrystallisation from methylene chloride/methanol. The neutral fumarate prepared from this product crystallises from methanol/ether; melting point 202°–203°.

EXAMPLE 5

Analogously to the procedure described in Example 3, trans-3-hydroxy-4-(p-methoxy-phenoxy)-1-carbobenzyloxy-pyrrolidine is obtained in the form of a pale yellow oil from 5.0 g (0.023 mol) of 3,4-epoxy-1-carbobenzyloxy-pyrrolidine and 5.7 g (0.046 mol) of hydroquinone monomethyl ether. After the hydrogenation, which is carried out analogously to Example 3, of 0.021 mol of this compound, trans-3-hydroxy-4-(p-methoxy-phenoxy)-pyrrolidine with a melting point of 126°–128° is obtained after recrystallisation of the crude base from methanol/ether. The neutral fumarate prepared from this product crystallises from methanol/ether; melting point 168°–169°.

EXAMPLE 6

Analogously to the procedure described in Example 3, trans-3-hydroxy-4-(1-naphthyloxy)-1-carbobenzyloxy-pyrrolodine with a melting point of 122°–124° is obtained from 5.0 g (0.023 mol) of 3,4-epoxy-1-carbobenzyloxy-pyrrolidine and 6.6 g (0.046 mol) of 1-naphthol, after recrystallisation of the product from methylene chloride/hexane. After the hydrogenation, which is carried out analogously to Example 3, of 0.015 mol of this compound, trans-3-hydroxy-4-(1-naphthyloxy)-pyrrolidine with a melting point of 116°–118° is obtained after recrystallisation of the crude base from methanol/ether. The neutral fumarate prepared from this product crystallises from methanol/ether; melting point 120°–122°.

EXAMPLE 7

Analogously to the procedure described in Example 3, trans-3-hydroxy-4-(o-methyl-phenoxy)-1-carbobenzyloxy-pyrrolidine is obtained from 10 g (0.046 mol) of 3,4-epoxy-1-carbobenzyloxy-pyrrolidine and 9.8 g (0.092 mol) of o-cresol; after recrystallisation from ether/hexane, the product is obtained in the form of crystals with a melting point of 80°–83°. After the hydrogenation, which is carried out analogously to Example 3, of 0.036 mol of this compound, trans-3-hydroxy-4-(o-methyl-phenoxy)-pyrrolidine with a melting point of 100°–103° is obtained after recrystallisation of the crude base from ether. The neutral fumarate prepared from this product crystallises from methanol/ether; melting point 82°–84°.

EXAMPLE 8

Analogously to the procedure described in Example 3, trans-3-hydroxy-4-(3,4-dimethyl-phenoxy)-1-carbobenzyloxy-pyrrolidine is obtained in the form of a pale yellow oil from 15 g (0.068 mol) of 3,4-epoxy-1-carbobenzyloxy-pyrrolidine and 16.7 g of 3,4-dimethylphenol. After the hydrogenation, which is carried out analogously to Example 3, of 0.012 mol of this compound, crystalline trans-3-hydroxy-4-(3,4-dimethylphenoxy)-pyrrolidine with a melting point of 97°–99° is obtained after recrystallisation of the crude product from methanol/ether. The neutral fumarate prepared from this product crystallises from methanol/ether; melting point 158°–159°.

EXAMPLE 9

21.4 g (0.06 mol) of the trans-3-hydroxy-4-(3,4-dimethylphenoxy)-1-carbobenzyloxy-piperidine described in Example 19 are dissolved in 4.8 g (0.06 mol) of pyridine and the solution is treated dropwise, at room temperature, with 18.4 g (0.18 mol) of acetic anhydride. After the addition has ended, the mixture is stirred at room temperature for 20 hours and then poured into 200 ml of ice water. The white product which has precipitated is filtered off, washed with water, then with methanol and finally with ether and dried at 40° under a high vacuum, whereupon trans-3-acetoxy-4-(3,4-dimethyl-phenoxy)-1-carbobenzyloxy-piperidine is obtained in the form of white crystals with a melting point of 109°–112°.

16.0 g (0.04 mol) of trans-3-acetoxy-4-(3,4-dimethyl-phenoxy)-1-carbobenzyloxy-piperidine are dissolved in 400 ml of methanol and hydrogenated in the presence of 1.5 g of a 5% strength palladium-on-charcoal catalyst under normal pressure. After the reaction has ended, the catalyst is filtered off by means of a layer of diatomaceous earth and the filtrate is evaporated under a water pump vacuum, whereupon trans-3-acetoxy-4-(3,4-dimethylphenoxy)-piperidine is obtained in the form of a yellow oil. Reaction of the base with fumaric acid in ethanol/ether gives the crystalline acid fumarate with a melting point of 170°–172°.

EXAMPLE 10

Analogously to the procedure described in Example 14, trans-3-hydroxy-4-(1-naphthyloxy)-1-carbobenzyloxy-piperidine is obtained in the form of a reddish oil from 17.5 g (0.075 mol) of 3,4-epoxy-1-carbobenzyloxy-piperidine and 21.6 g (0.15 mol) of 1-naphthol. The hydrogenation, which is carried out analogously to Example 14, of 0.05 mol of this compound gives trans-3-hydroxy-4-(1-naphthyloxy)-piperidine in the form of the crude base. The acid fumarate prepared therefrom with fumaric acid crystallises from methanol/ether; melting point 242°–244°.

EXAMPLE 11

Analogously to the procedure described in Example 2, trans-3-hydroxy-4-phenylthio-1-($\beta,\beta,\beta$-trichloroethoxycarbonyl)-pyrrolidine is obtained in the form of a yellow oil from 10.8 g (0.04 mol) of the 3,4-epoxy-1-($\beta,\beta,\beta$-trichloroethoxycarbonyl)-pyrrolidine described in Example 1b) and 8.8 g (0.08 mol) of thiophenol. After the treatment of 0.03 mol of this compound with zinc dust in glacial acetic acid, which treatment is carried out analogously to Example 2, trans-3-hydroxy-4-phenylthio-pyrrolidine is obtained after crystallisation of the product from methylene chloride/ether. The crystalline neutral fumarate with a melting point of 140°–141° is prepared by reacting the free base with a solution of fumaric acid in methanol/ether.

EXAMPLE 12

5.7 g (0.018 mol) of trans-3-hydroxy-4-chloro-1-($\beta,\beta,\beta$-trichloroethoxycarbonyl)-piperidine are dissolved in 60 ml of 90% strength acetic acid and the solution is treated, while cooling with an ice-water bath, with 4.7 g of zinc dust in portions and the reaction mixture is subsequently stirred for 3 hours at room temperature and then filtered through a layer of diatomaceous earth and the filtrate is evaporated to dryness under a high vacuum, crude trans-3-hydroxy-4-chloropiperidine being obtained as a white residue.

The resulting crude product is taken up in 300 ml of acetonitrile and the solution is heated together with 3.4 g (0.036 mol) of phenol and 100 ml of 2 N sodium hydroxide solution for 15 hours under reflux. The cooled reaction mixture is evaporated to about ⅓ of the original volume under a water pump vacuum, then diluted with water and extracted by shaking with 3 times 200 ml of methylene chloride. The organic phase is washed 3 times with 1 N sodium hydroxide solution and twice with a saturated aqueous solution of sodium chloride, dried over sodium sulphate and evaporated under a water pump vacuum. The oily residue is dissolved in a little chloroform and the solution is introduced on to a small silica gel column. Trans-3-hydroxy-4-phenoxy-piperidine is isolated by elution with a chloroform/methanol mixture (1:1), after evaporation of the solvent, and, with fumaric acid, this product forms a neutral fumarate with a melting point of 180°–183°.

Trans-3-hydroxy-4-chloro-1-($\beta,\beta,\beta$-trichloroethoxycarbonyl)-piperidine, which is used as the starting material, can be prepared as follows:

124.5 g (1.5 mol) of 1,2,5,6-tetrahydropyridine are dissolved in 1,200 ml of benzene. 124 g of sodium bicarbonate are introduced into this solution and the mixture is then cooled to 0° under a nitrogen atmosphere and, at this temperature, is treated slowly dropwise in the course of 3½ hours with a solution of 316 g (1.5 mol) of 2,2,2-trichloroethyl chloroformate in 250 ml of benzene. The resulting white suspension is subsequently stirred for a further 15 hours at 0° and then poured into 2,000 ml of ice-water. The benzene phase is separated off and the aqueous phase is extracted by shaking with twice 1,000 ml of methylene chloride; the combined organic phases are washed with 1 N hydrochloric acid and then with a saturated solution of sodium chloride, dried over sodium sulphate and evaporated under a water pump vacuum, whereupon 1-($\beta,\beta,\beta$-trichloroethoxycarbonyl)-1,2,5,6-tetrahydropyridine is obtained as a slightly reddish oil.

100 g (0.38 mol) of 1-($\beta,\beta,\beta$-trichloroethoxycarbonyl)-1,2,5,6-tetrahydropyridine are dissolved in 1,200 ml of methylene chloride and the solution is treated with 157 g (0.77 mol) of 85% strength m-chloroperbenzoic acid in portions. The slightly exothermic reaction is kept at room temperature by means of a water bath. After the addition has ended (which takes about 2 hours), the reaction mixture, in which a white suspension forms, is stirred for a further 15 hours at room temperature. The m-chlorobenzoic acid which has precipitated is filtered off and the filtrate is washed with a saturated aqueous solution of sodium carbonate, then with aqueous iron-II sulphate solution, then with 0.1 N sodium hydroxide solution and finally with water, dried over sodium sulphate and evaporated under a water pump vacuum. The oil which remains is dissolved in 100 ml of benzene and the solution is filtered through a layer of silica gel. Elution with a benzene/ethyl acetate mixture (1:1) and evaporation of the solvent gives pure 3,4-epoxy-1-($\beta,\beta,\beta$-trichloroethoxycarbonyl)-piperidine in the form of a slightly orange coloured oil.

5.0 g (0.018 mol) of 3,4-epoxy-1-($\beta,\beta,\beta$-trichloroethoxycarbonyl)-piperidine are dissolved in 50 ml of dioxane and the solution is treated with 60 ml of 6 N hydrochloric acid. The slightly exothermic reaction is kept at room temperature by means of a water bath, and the reaction mixture is stirred for 15 hours, then diluted with water and extracted with 3 times 100 ml of methylene chloride. The organic phase is washed with 0.1 N sodium hydroxide solution and then with a saturated aqueous solution of sodium chloride, dried over sodium sulphate and then evaporated to dryness, first under a water pump vacuum and then under a high vacuum, whereupon trans-3-hydroxy-4-chloro-1-($\beta,\beta,\beta$-trichloroethoxycarbonyl)-piperidine is obtained in the form of a slightly yellow oil.

EXAMPLE 13

40 g (0.146 mol) of the 3,4-epoxy-1-($\beta,\beta,\beta$-trichloroethoxycarbonyl)-piperidine obtained according to Example 12 are dissolved, together with 32 g (0.29 mol) of thiophenol and 146 ml (0.29 mol) of 2 N sodium hydroxide solution, in 300 ml of acetonitrile. The reaction mixture is heated under reflux for 4 hours, then cooled to room temperature and concentrated to about ⅓ of the original volume under a water pump vacuum. The solution is then diluted with 900 ml of water and extracted by shaking with 3 times 1,000 ml of methylene chloride; the combined organic phases are washed twice with 0.1 N sodium hydroxide solution and then with water, dried over sodium sulphate and evaporated under a water pump vacuum. The oil which remains is dissolved in 50 ml of benzene and the solution is filtered through a layer of silica gel. Trans-3-hydroxy-4-phenylthio-1-($\beta,\beta,\beta$-trichloroethoxycarbonyl)-piperidine is isolated in the form of a slightly orange coloured oil by elution with a benzene/ethyl acetate mixture (4:1).

14.0 g (0.036 mol) of trans-3-hydroxy-4-phenylthio-1-($\beta,\beta,\beta$-trichloroethoxycarbonyl)-piperidine are dissolved in 140 ml of 90% acetic acid and the solution is treated with 9.5 g (0.14 mol) of zinc dust in portions. The reaction mixture is subsequently stirred for one hour at room temperature and then filtered through a layer of diatomaceous earth. The filtrate is evaporated under a high vacuum, the resulting residue is taken up in 500 ml of water, the solution is cooled to 0° in an ice-water bath and, at this temperature, rendered strongly alkaline with concentrated sodium hydroxide solution and the reaction mixture is extracted by shaking with 3 times 200 ml of methylene chloride. The combined organic phases are washed once with water, dried over sodium sulphate and evaporated under a water pump vacuum, whereupon trans-3-hydroxy-4-phenylthio-piperidine is obtained in the form of the crystalline crude base, which is recrystallised from methanol/ether; melting point 135°–136°. The neutral fumarate prepared from the base with fumaric acid crystallises from methanol/ether; melting point 171°–173°.

EXAMPLE 14

8.2 g (0.025 mol) of trans-3-hydroxy-4-phenoxy-1-carbobenzyloxy-piperidine are dissolved in 140 ml of methanol and hydrogenated in the presence of 0.8 g of a 5% strength palladium-on-charcoal catalyst under normal pressure and at room temperature. After the absorption of hydrogen has ceased, the catalyst is filtered off by means of diatomaceous earth and the filtrate is evaporated under a water pump vacuum. The crude base crystallises from methanol/ether and gives trans-3-hydroxy-4-phenoxy-piperidine with a melting point of 134°–136°. The neutral fumarate prepared therefrom with fumaric acid crystallises from methanol/ether; melting point 180°–183°.

Trans-3-hydroxy-4-phenoxy-1-carbobenzyloxy-piperidine, which is used as the starting material, can be prepared as follows:

(a) 83.1 g (1 mol) of 1,2,5,6-tetrahydropyridine are dissolved in 300 ml of benzene. 83 g of sodium bicarbonate are introduced into this solution and the mixture is cooled to 0° under a nitrogen atmosphere and, at this temperature, treated dropwise in the course of one hour with 332 ml of a 50% strength solution of benzyl chloroformate in toluene (1 mol). The reaction mixture is stirred at 0° for a further 2½ hours and then poured into 1.5 liters of ice-water. The benzene phase is separated off and the aqueous phase is extracted by shaking 3 times with 250 ml of methylene chloride; subsequently the combined organic phases are washed with 1 N hydrochloric acid and then with a saturated solution of sodium chloride, dried over sodium sulphate and evaporated under a water pump vacuum. The oily residue is distilled under a high vacuum and gives 1-carbobenzyloxy-1,2,5,6-tetrahydropyridine with a boiling point of 102°–113°/0.01 mm Hg.

(b) 108.5 g (0.5 mol) of 1-carbobenzyloxy-1,2,5,6-tetrahydropyridine are dissolved in 1,000 ml of dichloroethane and the solution is treated with 182 g (0.9 mol) of 85% strength m-chloro-perbenzoic acid in portions. The slightly exothermic reaction is kept at room temperature by means of a water bath. After the addition has ended, the reaction mixture, in which a white suspension forms, is stirred for a further 48 hours at room temperature, the m-chloro-benzoic acid which has precipitated is filtered off, the filtrate is washed successively with a saturated solution of sodium carbonate, then with iron-II sulphate solution, then with 0.1 N sodium hydroxide solution and finally with water, and the organic phase is dried over sodium sulphate and evaporated under a water pump vacuum. 3,4-Epoxy-1-carbobenzyloxy-piperidine, which remains behind as a yellowish oil, is a single compound according to spectroscopy and thin layer chromatography and can be used for further reactions without further purification. When this compound is distilled under a high vacuum at the boiling point of 145°–146°/0.4 mm Hg, partial decomposition takes place.

(c) 23.3 g (0.1 mol) of 3,4-epoxy-1-carbobenzyloxy-piperidine are dissolved, together with 18.8 g (0.2 mol) of phenol and 100 ml of 2 N sodium hydroxide solution (0.2 mol) in 400 ml of acetonitrile. The reaction mixture is heated under reflux for 7 hours, then cooled to room temperature and concentrated to about ⅓ of the volume under a water pump vacuum. The solution is then diluted with 500 ml of water and extracted by shaking with 3 times 100 ml of methylene chloride and the organic phase is washed with 2 N sodium hydroxide solution and then with water, dried over sodium sulphate and evaporated under a water pump vacuum. The residue obtained is an oil which contains, in addition to the main product, i.e. trans-3-hydroxy-4-phenoxy-1-carbobenzyloxy-piperidine, about 5% of the isomer trans-3-phenoxy-4-hydroxy-1-carbobenzyloxy-piperidine.

For identification, the two isomers can be separated from one another by column chromatography on silica gel using benzene-ethyl acetate as the eluant.

EXAMPLE 15

Analogously to the procedure described in Example 14, crystalline trans-3-hydroxy-4-(2-methyl-4-carbamoyl-phenoxy)-1-carbobenzyloxy-piperidine with a melting point of 175°–177° is obtained from 11.6 g (0.05 mol) of 3,4-epoxy-1-carbobenzyloxy-piperidine and 15.1 g (0.1 mol) of 3-methyl-4-hydroxybenzamide. After the hydrogenation, which is carried out analogously to Example 14, of 0.018 mol of this product, trans-3-hydroxy-4-(2-methyl-4-carbamoyl-phenoxy)-piperidine is obtained and this is recrystallized from methanol/ether; melting point 210°–212°. An amorphous neutral fumarate can be obtained from the base using fumaric acid.

EXAMPLE 16

Analogously to the procedure described in Example 14, trans-3-hydroxy-4-(p-methoxy-phenoxy)-1-carbobenzyloxy-piperidine is obtained in the form of a reddish oil from 23.3 g (0.1 mol) of 3,4-epoxy-1-carbobenzyloxy-piperidine and 24.8 g (0.2 mol) of hydroquinone monomethyl ether. The hydrogenation, which is carried out analogously to Example 14, of 0.075 mol of this product gives trans-3-hydroxy-4-(p-methoxyphenoxy)-piperidine with a melting point of 154°–156°, after crystallisation of the crude product from methanol/ether. The neutral fumarate prepared from this product with fumaric acid crystallises from methanol/ether; melting point 171°–173°.

EXAMPLE 17

Analogously to the procedure described in Example 14, trans-3-hydroxy-4-(o-methoxy-phenoxy)-1-carbobenzyloxy-piperidine is obtained in the form of a yellowish oil from 15.0 g (0.064 mol) of 3,4-epoxy-1-carbobenzyloxy-piperidine and 19.9 g (0.16 mol) of guaiacol. The hydrogenation, which is carried out analogously to Example 14, of 0.049 mol of this product gives crystalline trans-3-hydroxy-4-(o-methoxyphenoxy)-piperidine. The base is converted into the corresponding crystalline hydrochloride by treatment with an ethereal solution of hydrogen chloride, and after recrystallisation from methanol/ether this hydrochloride melts at 213°–215°.

EXAMPLE 18

Analogously to the procedure described in Example 14, an oily crude product is obtained from 9.3 g (0.04 mol) of 3,4-epoxy-1-carbobenzyloxy-piperidine and 12.3 g (0.08 mol) of 3,4-dimethoxy-phenol, and this product, dissolved in a little benzene, is purified on a silica gel column with subsequent elution with a benzene/ethyl acetate mixture (4:1) and gives pure trans-3-hydroxy-4-(3,4-dimethoxy-phenoxy)-1-carbobenzyloxy-piperidine. Hydrogenation, which is carried out analogously to Example 14 with 0.014 mol of this compound, gives trans-3-hydroxy-4-(3,4-dimethoxy-phenoxy)-piperidine. The neutral fumarate prepared therefrom with fumaric acid crystallises from methanol/ether; melting point 173°–175°.

EXAMPLE 19

Analogously to the procedure described in Example 14, a mixture of trans-3-hydroxy-4-(3,4-dimethyl-phenoxy)-1-carbobenzyloxy-piperidine and trans-4-hydroxy-3-(3,4-dimethylphenoxy)-1-carbobenzyloxy-piperidine is obtained in the form of a yellowish oil from 116.5 g (0.5 mol) of 3,4-epoxy-1-carbobenzyloxy-piperidine and 122 g (1 mol) of 3,4-dimethylphenol. The two isomers are separated by column chromatography on silica gel using, as the eluant, benzene to which gradually increasing amounts of ethyl acetate are added, trans-3-hydroxy-4-(3,4-dimethylphenoxy)-1-carbobenzyloxy-piperidine being isolated as the first main fraction and as the main product, and pure trans-4-hydroxy-3-(3,4-dimethylphenoxy)-1-carbobenzyloxy-piperidine being isolated last, afer mixed fractions. Both isomers are obtained in the form of pale yellow oils.

The hydrogenation, which is carried out analogously to Example 14, of 71.8 g (0.2 mol) of trans-3-hydroxy-4-(3,4-dimethylphenoxy)-1-carbobenzyloxy-piperidine gives trans-3-hydroxy-4-(3,4-dimethylphenoxy)-piperidine which crystallises from methanol/ether; melting point 125°–127°. The acid fumarate prepared with fumaric acid crystallises from ethanol/ether; melting point 175°–177°.

The hydrogenation, which is carried out analogously to Example 14, of 7.5 g (0.022 mol) of trans-4-hydroxy-3-(3,4-dimethylphenoxy)-1-carbobenzyloxy-piperidine gives trans-4-hydroxy-3-(3,4-dimethylphenoxy)-piperidine with a melting point of 93°–95°, after crystallisation of the crude product from methanol/ether. The hydrochloride prepared from this product by reaction with an ethereal solution of hydrogen chloride crystallises from methanol/ether; melting point 160°–163°.

EXAMPLE 20

8.85 g (0.04 mol) of the trans-3-hydroxy-4-(3,4-dimethylphenoxy)-piperidine described in Example 19 are dissolved in 20 ml of formic acid and the solution is treated with 10 ml of a 35% strength aqueous solution of formaldehyde. The mixture is heated at 80° for 4 hours and, after cooling, is then evaporated under a high vacuum. The residue is dissolved in 100 ml of methanol and the solution is acidified with an approximately 6 N solution of hydrogen chloride in ethanol. The solvent is evaporated under a water pump vacuum, the oily residue is dissolved in 300 ml of water and the solution is extracted by shaking with twice 50 ml of methylene chloride. The aqueous phase is rendered strongly alkaline with concentrated sodium hydroxide solution and then extracted with 3 times 100 ml of methylene chloride. The organic phase is washed once with water, dried over sodium sulphate and evaporated to dryness under a water pump vacuum. The oil which remains is dissolved in an excess of an ethanolic solution of hydrogen chloride and the hydrochloride is precipitated with ether, amorphous trans-3-hydroxy-4-(3,4-dimethyl-phenoxy)-1-methyl-piperidine hydrochloride being obtained.

EXAMPLE 21

Analogously to the procedure described in Example 14, an oily crude product is obtained from 15.0 g (0.064 mol) of 3,4-epoxy-1-carbobenzyloxy-piperidine and 16.5 g (0.12 mol) of m-chloro-phenol and this product, dissolved in benzene, is filtered through silica gel and, after evaporation of the solvent, gives trans-3-hydroxy- 4-(m-chloro-phenoxy)-1-carbobenzyloxy-piperidine. Hydrogenation, which is carried out analogously to Example 14 with 0.039 mol of this compound, gives crystalline trans-3-hydroxy-4-(m-chlorophenoxy)-piperidine with a melting point of 109°–111°. The acid fumarate obtained therefrom with fumaric acid crystallises from methanol/acetone; melting point 138°–140°.

EXAMPLE 22

Analogously to the procedure described in Example 14, an oily crude product is obtained from 15.0 g (0.064 mol) of 3,4-epoxy-1-carbobenzyloxy-piperidine and 21.0 g (0.12 mol) of 3,4-dichlorophenol and this product, dissolved in benzene, is filtered through silica gel and gives trans-3-hydroxy-4-(3,4-dichlorophenoxy)-1-carbobenzyloxy-piperidine. Hydrogenation, which is carried out analogously to Example 14 with 0.036 mol of this product, gives crystalline trans-3-hydroxy-4-(3,4-dichlorophenoxy)-piperidine with a melting point of 196°–198°. The acid fumarate prepared therefrom with fumaric acid crystallises from methanol/ether; melting point 180°–182°.

EXAMPLE 23

Analogously to the procedure described in Example 20, trans-3-hydroxy-4-phenylthio-1-methyl-piperidine is obtained in the form of a yellow oil from 5.2 g (0.025 mol) of the trans-3-hydroxy-4-phenylthio-piperidine described in Example 13 by reaction with formaldehyde and formic acid. The acid fumarate prepared from this product with fumaric acid crystallises from methanol/ether; melting point 150°–152°.

EXAMPLE 24

A solution of 45 g (0.12 mol) of the trans-3-hydroxy-4-(3,4-dimethyl-phenoxy)-1-carbobenzyloxy-piperidine described in Example 19 in 100 ml of dimethylformamide is introduced in the course of 30 minutes, at 30°–35°, into a suspension of 8.15 g (0.18 mol) of a 55% strength oily dispersion of sodium hydride in 100 ml of dimethylformamide. The mixture is then warmed to 50° and treated dropwise with 22.5 g (0.15 mol) of methyl iodide. The reaction mixture is subsequently stirred for 3 hours at 60°–70° and for 15 hours at room temperature, then poured into 600 ml of ice-water and extracted by shaking with 3 times 150 ml of ethyl acetate. The combined organic phases are washed once with water, dried over sodium sulphate and evaporated to dryness, first under a water pump vacuum and then under a high vacuum. This gives trans-3-methoxy-4-(3,4-dimethyl-phenoxy)-1-carbobenzyloxy-piperidine in the form of a pale yellow oil.

36.9 g (0.1 mol) of trans-3-methoxy-4-(3,4-dimethyl-phenoxy)-1-carbobenzyloxy-piperidine are dissolved in 800 ml of methanol and hydrogenated in the presence of 6 g of a 5% strength palladium-on-charcoal catalyst under normal pressure and at room temperature. After the absorption of hydrogen has ceased, the catalyst is filtered off over a layer of diatomaceous earth and the filtrate is evaporated under a water pump vacuum. This gives trans-3-methoxy-4-(3,4-dimethyl-phenoxy)-piperidine in the form of a yellowish oil. The acid fumarate prepared therefrom with fumaric acid crystallises from methanol/ether; melting point 137°–139°.

EXAMPLE 25

Analogously to the procedure described in Example 20, trans-3-methoxy-4-(3,4-dimethylphenoxy)-1-methyl-piperidine is obtained in the form of a pale yellow oil from 4.7 g (0.02 mol) of the trans-3-methoxy-4-(3,4-dimethylphenoxy)-piperidine obtained according to Example 24, by reaction with formaldehyde and formic acid. The acid fumarate obtained from this product with fumaric acid crystallises from methanol/ether; melting point 151°–153°.

EXAMPLE 26

7.8 g (0.035 mol) of the trans-3-hydroxy-4-(3,4-dimethylphenoxy)-piperidine described in Example 19 are dissolved in a suspension of 8 g of potassium carbonate in 150 ml of methanol and the solution is treated dropwise with 6.3 g (0.053 mol) of propargyl bromide at room temperature. The reaction mixture is stirred for a further 20 hours at this temperature and then filtered and the filtrate is evaporated under a water pump vacuum. The oily residue is dissolved in 200 ml of toluene, the solution is extracted with 3 times 150 ml of 1 N hydrochloric acid and the combined aqueous phases are rendered alkaline with concentrated sodium hydroxide solution, while cooling with ice, and extracted with twice 200 ml of chloroform. The organic phase is washed a further once with water, dried over sodium sulphate and evaporated to dryness under a water pump vacuum. The resulting oil is dissolved in 50 ml of chloroform and the solution is filtered through a layer of silica gel. By elution with chloroform, crystalline trans-3-hydroxy-4-(3,4-dimethylphenoxy)-1-propargylpiperidine with a melting point of 105°–107° is obtained from the filtrate, after removal of the solvent under a water pump vacuum.

The hydrochloride prepared from the base by treatment with an approximately 6 N solution of hydrogen chloride in ether crystallises from ethanol/ether; melting point 140°–142°.

EXAMPLE 27

Analogously to the procedure described in Example 20, trans-4-hydroxy-3-(3,4-dimethyl-phenoxy)-1-methyl-piperidine with a melting point of 98°–99° is obtained from 4.9 g (0.02 mol) of the trans-4-hydroxy-3-(3,4-dimethyl-phenoxy)-piperidine obtained according to Example 19, by reaction with formaldehyde and formic acid. Treatment of the base with an approximately 6 N solution of hydrogen chloride in ether gives an amorphous hydrochloride.

EXAMPLE 28

Analogously to the procedure described in Example 14c), trans-3-hydroxy-4-(4-benzyloxy-phenoxy)-1-carbobenzyloxy-piperidine is obtained in the form of an oily product from 30.0 g (0.12 mol) of 3,4-epoxy-1-carbobenzyloxy-piperidine and 51.4 g (0.25 mol) of hydroquinone monobenzyl ether.

Hydrogenation, which is carried out analogously to Example 14 with 0.06 mol of this product, gives trans-3-hydroxy-4-(4-hydroxy-phenoxy)-piperidine, which is crystallised from methanol/ether; melting point 176°–178°. Reaction with fumaric acid gives a neutral fumarate which crystallises from methanol/ether and has a melting point of 231°–232°.

EXAMPLE 29

Analogously to the procedure described in Example 14c), trans-3-hydroxy-4-(5,6,7,8-tetrahydro-2-naphthyloxy)-1-carbobenzyloxy-piperidine is obtained from 23.3 g (0.1 mol) of 3,4-epoxy-1-carbobenzyloxy-piperidine and 28.9 g (0.195 mol) of 5,6,7,8-tetrahydro-2-naphthol.

Hydrogenation, carried out analogously to Example 14 with 0.08 mol of this product, gives trans-3-hydroxy-4-(5,6,7,8-tetrahydro-2-naphthyloxy)-piperidine. The base is crystallised from methanol/ether and has a melting point of 125°–127° and on reaction with fumaric acid gives a neutral fumarate which crystallises from methanol/ether and has a melting point of 202°–203°.

EXAMPLE 30

Analogously to the procedure described in Example 14, an oily crude product is obtained from 17.5 g (0.075 mol) of 3,4-epoxy-1-carbobenzyloxy-piperidine and 20.8 g (0.15 mol) of p-nitro-phenol and this product is dissolved in benzene and the solution is filtered through a layer of silica gel. Elution with a benzene/ethyl acetate mixture (1:1) and evaporation of the solvent gives pure trans-3-hydroxy-4-(p-nitrophenoxy)-1-carbobenzyloxy-piperidine. 4.1 g (0.01 mol) of this compound are dissolved in 15 ml of glacial acetic acid and the solution is introduced dropwise into 15 ml of a 40% strength solution of hydrobromic acid in glacial acetic acid. A slightly exothermic reaction takes place and a white precipitate forms and this is filtered off after stirring for 3 hours at room temperature and is trans-3-hydroxy-4-(p-nitrophenoxy)-piperidine hydrobromide with a melting point of 248°–250°. The base is set free from the hydrobromide by treatment with an aqueous solution of ammonia; with fumaric acid the base forms an acid fumarate which crystallises from methanol/ether; melting point 179°–180°.

EXAMPLE 31

Analogously to the procedure described in Example 14c), trans-3-hydroxy-4-(p-fluoro-phenoxy)-1-carbobenzyloxy-piperidine is obtained in the form of a yellowish oil from 17.5 g (0.075 mol) of 3,4-epoxy-1-carbobenzyloxy-piperidine and 16.8 g (0.15 mol) of p-fluoro-phenol.

Hydrogenation, which is carried out analogously to Example 14 with 0.05 mol of this compound, gives trans-3-hydroxy-4-(p-fluoro-phenoxy)-piperidine in the form of the crude base, which crystallises from methanol/ether; melting point 121°–123°. The acid fumarate prepared from this product with fumaric acid crystallises from methanol/ether; melting point 159°–161°.

EXAMPLE 32

A solution of 21.3 g (0.05 mol) of the trans-4-hydroxy-3-(3,4-dimethyl-phenoxy)-1-carbobenzyloxy-piperidine described in Example 19 in 50 ml of dimethylformamide is introduced in the course of 30 minutes, at 30°–35°, into a suspension of 3.6 g (0.08 mol) of a 55% strength oily dispersion of sodium hydride in 50 ml of dimethylformamide. The mixture is then warmed to 50° and treated dropwise with 9.94 g (0.07 mol) of methyl iodide. The reaction mixture is subsequently stirred for 3 hours at 60°–70° and for 15 hours at room temperature, then poured into 600 ml of ice-water and extracted by shaking with 3 times 150 ml of ethyl acetate. The combined organic phases are washed once with water, dried over sodium sulphate and evaporated to dryness, first under a water pump vacuum and then under a high vacuum. This gives trans-4-methoxy-3-(3,4-dimethylphenoxy)-1-carbobenzyloxy-piperidine in the form of a pale yellow oil.

15.0 g (0.04 mol) of trans-4-methoxy-3-(3,4-dimethylphenoxy)-1-carbobenzyloxy-piperidine are dissolved in 180 ml of methanol and hydrogenated in the presence of 1.0 g of a 5% strength palladium-on-charcoal catalyst under normal pressure and at room temperature. After the absorption of hydrogen has ceased, the catalyst is filtered off over a layer of diatomaceous earth and the filtrate is evaporated under a water pump vacuum. This gives trans-4-methoxy-3-(3,4-dimethyl-phenoxy)-piperidine in the form of a yellowish oil. Treatment of the base with an approximately 6 N solution of hydrogen chloride in ether gives an amorphous hydrochloride.

EXAMPLE 33

Analogously to the procedure described in Example 14c), trans-3-hydroxy-4-(5,6,7,8-tetrahydro-1-naphthyloxy)-1-carbobenzyloxy-piperidine is obtained as an oily product from 23.3 g (0.1 mol) of 3,4-epoxy-1-carbobenzyloxy-piperidine and 28.9 g (0.195 mol) of 5,6,7,8-tetrahydro-1-naphthol. Hydrogenation, which is carried out analogously to Example 14 with 26.6 g (0.07 mol) of this product, gives trans-3-hydroxy-4-(5,6,7,8-tetrahydro-1-naphthyloxy)-piperidine, which is recrystallised from methanol/ether and has a melting point of 168°–169°; reaction with fumaric acid gives a neutral fumarate which crystallises from methanol/ether and has a melting point of 208°–210°.

EXAMPLE 34

Analogously to the procedure described in Example 14c), trans-3-hydroxy-4-(2,3-dimethylphenoxy)-1-carbobenzyloxy-piperidine is obtained in the form of a brownish oil from 50 g (0.21 mol) of 3,4-epoxy-1-carbobenzyloxy-piperidine and 53.8 g (0.42 mol) of 2,3-dimethyl-phenol.

Hydrogenation, which is carried out analogously to Example 14 with 50.8 g (0.143 mol) of this product, gives trans-3-hydroxy-4-(2,3-dimethylphenoxy)-piperidine. The base is crystallized from methanol/ether and has a melting point of 127°–129° and on reaction with fumaric acid gives a neutral fumarate which crystallises from methanol/ether; melting point 176°–178°.

EXAMPLE 35

Analogously to the procedure described in Example 14c), trans-3-hydroxy-4-(2,6-dimethyl-phenoxy)-1-carbobenzyloxy-piperidine is obtained in the form of a yellow oil from 15.0 g (0.064 mol) of 3,4-epoxy-1-carbobenzyloxy-piperidine and 15.5 g (0.12 mol) of 2,6-dimethylphenol.

Hydrogenation, which is carried out analogously to Example 14 with 8.3 g (0.023 mol) of this product, gives crystalline trans-3-hydroxy-4-(2,6-dimethylphenoxy)-piperidine. The base can be crystallized from methanol/ether and has a melting point of 131°–133° and on reaction with fumaric acid gives an acid fumarate which crystallises from methanol/ether; melting point 178°–180°.

EXAMPLE 36

Analogously to the procedure described in Example 14c), trans-3-hydroxy-4-(p-tert.-butylphenoxy)-1-carbobenzyloxy-piperidine is obtained in the form of a yellowish oil from 20.0 g (0.085 mol) of 3,4-epoxy-1-carbobenzyloxy-piperidine and 25.8 g (0.17 mol) of 4-tert.-butyl-phenol.

Hydrogenation, which is carried out analogously to Example 14 with 20.0 g (0.052 mol) of this product, gives trans-3-hydroxy-4-(p-tert.-butylphenoxy)-piperidine in the form of a yellowish oil. The base can be crystallised from methanol/ether and has a melting point of 138°–140° and on treatment with fumaric acid gives an acid fumarate which crystallises from methanol; melting point 192°–194°.

EXAMPLE 37

Analogously to the procedure described in Example 3, trans-3-hydroxy-4-(m-chlorophenoxy)-1-carbobenzyloxy-pyrrolidine is obtained in the form of a yellow oil from 25.0 g (0.114 mol) of 3,4-epoxy-1-carbobenzyloxy-pyrrolidine and 29.3 g (0.228 mol) of m-chlorophenol. After the hydrogenation, which is carried out analogously to Example 3, of 32.0 g (0.092 mol) of this compound, trans-3-hydroxy-4-(m-chlorophenoxy)-pyrrolidine is obtained in the form of a yellowish oil. The acid fumarate prepared therefrom crystallises from methanol/ether; melting point 128°–129°.

EXAMPLE 38

Analogously to the procedure described in Example 3, trans-3-hydroxy-4-(3,5-dimethylphenoxy)-1-carbobenzyloxy-pyrrolidine is obtained in the form of a yellow oil from 40.0 g (0.18 mol) of 3,4-epoxy-1-carbobenzyloxy-pyrrolidine and 44.7 g (0.366 mol) of 3,5-dimethylphenol.

After the hydrogenation, which is carried out analogously to Example 3, of 7.6 g (0.02 mol) of this compound, trans-3-hydroxy-4-(3,5-dimethylphenoxy)-pyrrolidine is obtained in the form of a yellow oil. The acid fumarate prepared therefrom crystallises from methanol/ether; melting point 178°–179°.

EXAMPLE 39

Analogously to the procedure described in Example 14c) trans-3-hydroxy-4-(2-bromo-4-methoxy-phenoxy)-1-carbobenzyloxy-piperidine is obtained as an oily product from 16.2 g (0.07 mol) of 3,4-epoxy-1-carbobenzyloxy-piperidine and 28.4 g (0.14 mol) of 2-bromo-4-methoxy-phenol.

Hydrogenation, which is carried out analogously to Example 14 with 17.6 g (0.04 mol) of this product, gives trans-3-hydroxy-4-(2-bromo-4-methoxy-phenoxy)-piperidine in the form of the crystalline base with a melting point of 132°–135° (from methylene chloride). The acid fumarate formed therefrom by treatment with fumaric acid crystallises from methanol/ether; melting point 200°–202°.

EXAMPLE 40

3.45 g (0.011 mol) of trans-4-hydroxy-5-(2,3-dimethylphenoxy)-1-methylsulphonyl-tetrahydro-1H-azepine are dissolved in 75 ml of dry benzene and the solution is treated in a nitrogen atmosphere with 15 ml of a 70% strength solution of sodium bis-2-methoxyethoxy-aluminium hydride in benzene. The reaction mixture is heated under reflux for 15 hours, then cooled to 0° in an ice-water bath and treated dropwise with 15 ml of water. The aluminium salt which has precipitated is filtered off and washed with benzene. The filtrate is evaporated to dryness under a water pump vacuum. The resulting crude trans-4-hydroxy-5-(2,3-dimethylphenoxy)-hexahydro-1H-azepine is converted into the hydrochloride by treatment with a 6 N solution of hydrogen chloride in ether and the hydrochloride is crystallised from ether/ethyl acetate; melting point 113°–115°.

Analogously, trans-4-hydroxy-5-phenoxy-hexahydro-1H-azepine and its hydrochloride are obtained from 3.14 g (0.011 mol) of trans-4-hydroxy-5-phenoxy-1-methylsulphonyl-hexahydro-1H-azepine, trans-4-hydroxy-5-(3,4-dimethyl-phenoxy)-hexahydro-1H-azepine and its hydrochloride are obtained from 3.45 g (0.011 mol) of trans-4-hydroxy-5-(3,4-dimethyl-phenoxy)-1-methylsulphonyl-hexahydro-1H-azepine, trans-4-hydroxy-5-(3,4-dichloro-phenoxy)-hexahydro-1H-azepine and its hydrochloride are obtained from 3.9 g (0.011 mol) of trans-4-hydroxy-5-(3,4-dichloro-phenoxy)-1-methylsulphonyl-hexahydro-1H-azepine and trans-4-hydroxy-5-(p-trifluoromethyl-phenoxy)-hexahydro-1H-azepine and its hydrochloride are obtained from 3.9 g (0.011 mol) of trans-4-hydroxy-5-(p-trifluoromethylphenoxy)-1-methylsulphonyl-hexahydro-1H-azepine.

The starting materials can be prepared as follows:

(a) 15.9 g (0.05 mol) of endo-4-(p-toluenesulphonyloxy-1-azabicyclo[3.2.1]octane hydrochloride with a melting point of 146°–148°, which, according to W. Kunz, Thesis, University of Basel 1973, 6349, page 92, can be obtained by reacting endo-1-azabicyclo[3.2.1]octan-4-ol, which is described in this thesis and in J. Org. Chem. 33, 4376–4380 (1968), with the approximately 1.2-fold molar amount of p-toluenesulphonyl chloride in absolute chloroform at room temperature for a reaction period of about 48 hours, precipitating the crude product with pentane and recrystallising the product from chloroform, and 23.0 g (0.2 mol) of methanesulphonyl chloride are stirred in 1,400 ml of 0.75 N sodium hydroxide solution for 4 hours at room temperature and the mixture is then heated at 90° for 20 minutes, while stirring. After cooling, the reaction mixture is extracted four times with methylene chloride. The combined extracts are washed with 0.1 N hydrochloric acid, dried over potassium carbonate and evaporated and 1-methylsulphonyl-2,3,6,7-tetrahydro-1H-azepine is obtained; melting point 95°–96° (from ethyl acetate/benzene).

(b) 11.7 g (0.067 mol) of 1-methanesulphonyl-2,3,6,7-tetrahydro-1H-azepine are dissolved in 230 ml of methylene chloride and the solution is treated with 23 g (0.13 mol) of m-chloro-perbenzoic acid in portions. A white suspension soon forms and this is stirred for a further 24 hours at room temperature. The m-chlorobenzoic acid which has precipitated is filtered off and the filtrate is washed with a saturated aqueous solution of sodium carbonate, then with aqueous iron-II sulphate solution, then with 0.1 N sodium hydroxide solution and finally with water and dried over sodium sulphate. On concentrating the solution under a water pump vacuum, white crystals of 1-methanesulphonyl-hexahydro-4,5-epoxy-1H-azepine are obtained and these are isolated by filtration; melting point 133°–134°.

(c) 7.0 g (0.036 mol) of 1-methanesulphonyl-hexahydro-4,5-epoxy-1H-azepine are dissolved, together with 8.9 g (0.073 mol) of 2,3-dimethyl-phenol, with 36.6 ml of 2 N sodium hydroxide solution (0.013 mol) in 200 ml of acetonitrile. The reaction mixture is heated under reflux for 5 days, then cooled to room temperature and concentrated under a water pump vacuum. The residue is then dissolved in 200 ml of methylene chloride and the organic phase is washed with three times 100 ml of 2 N sodium hydroxide solution and then with water, dried over sodium sulphate and evaporated under a water pump vacuum. The resulting crude product is purified by preparative thick layer chromatography (100×20 cm silica gel plates, layer thickness 1.5 mm). Crystalline trans-4-hydroxy-5-(2,3-dimethylphenoxy)-1-methanesulphonyl-hexahydro-1H-azepine with a melting point of 112°–115° is obtained by elution with a 3:1 mixture of toluene/ethyl acetate.

Analogously, trans-4-hydroxy-5-(3,4-dimethylphenoxy)-1-methanesulphonyl-hexahydro-1H-azepine is obtained using 6.9 g (0.073 mol) of 3,4-dimethylphenol, trans-4-hydroxy-5-(3,4-dichloro-phenoxy)-1-methanesulphonyl-hexahydro-1H-azepine is obtained using 11.9 g (0.073 mol) of 3,4-dichloro-phenol and trans-4-hydroxy-5-(p-trifluoromethyl-phenoxy)-1-methanesulphonyl-hexahydro-1H-azepine is obtained using 12.0 g (0.073 mol) of p-trifluoromethyl-phenol.

EXAMPLE 41

Analogously to the procedure described in Example 20, trans-3-hydroxy-4-(2,3-dimethylphenoxy)-1-methyl-piperidine is obtained in the form of an amorphous foam from 5.6 g (0.025 mol) of the trans-3-hydroxy-4-(2,3-dimethylphenoxy)-piperidine described in Example 34, by reaction with formaldehyde and formic acid. Treatment of the base with an approximately 6 N solution of hydrogen chloride in ether gives an amorphous hydrochloride.

EXAMPLE 42

Analogously to the procedure described in Example 20, trans-3-hydroxy-4-(2-bromo-4-methoxy-phenoxy)-1-methyl-piperidine is prepared from 3.63 g (0.012 mol) of the trans-3-hydroxy-4-(2-bromo-4-methoxy-phenoxy)-piperidine described in Example 39, by reaction with formaldehyde and formic acid. Treatment of the base with an approximately 6 N solution of hydrogen chloride in ether gives the hydrochloride thereof.

EXAMPLE 43

15.0 g (0.045 mol) of the trans-3-hydroxy-4-phenoxy-1-carbobenzyloxy-piperidine described in Example 14 are dissolved, together with 28.34 g (0.13 mol) of dicyclohexylcarbodiimide and 3.7 ml (0.045 mol) of pyridine, in 80 ml of dry dimethylsulphoxide. The mixture is cooled to 0° with an ice-water bath and treated with 2.6 g (0.023 mol) of trifluoroacetic acid. The cooling bath is removed again and the reaction mixture is stirred for a further 4 hours at room temperature in a nitrogen atmosphere. The white suspension is diluted with 250 ml of ethyl acetate and treated dropwise with a solution of 12.3 g (0.13 mol) of oxalic acid in 200 ml of methanol. After the evolution of gas has ceased, the reaction mixture is cooled to 0° in an ice-water bath and diluted with 400 ml of water and the dicyclohexylurea which has precipitated is separated off. The aqueous phase of the filtrate is extracted with 250 ml of ethyl acetate and the combined organic phases are dried over sodium sulphate and evaporated to dryness under a water pump vacuum. The resulting crude product is dissolved in benzene and the solution is filtered through a layer of silica gel. 4-Phenoxy-1-carbobenzyloxy-3-piperidone is obtained in the form of a pale yellow oil by elution with a benzene/ethyl acetate mixture (95:5).

14.0 g of this compound are dissolved in 150 ml of methanol and the solution is treated with 16.8 ml of a 2.5 N solution of hydrogen chloride in methanol and hydrogenated in the presence of 2.0 g of a 5% strength palladium-on-charcoal catalyst under normal pressure and at room temperature. After the absorption of hydrogen has ceased, the catalyst is filtered off by means of diatomaceous earth and the filtrate is evaporated under a water pump vacuum. The amorphous crude product can be crystallised in an acetone/ether mixture and gives 4-phenoxy-3-piperidone hydrochloride monohydrate in the form of white crystals; melting point 112°–115°.

EXAMPLE 44

Analogously to the procedure described in Example 43, 4-(3,4-dimethyl-phenoxy)-1-carbobenzyloxy-3-piperidone is obtained in the form of a yellow oil from 20.0 g (0.056 mol) of the trans-3-hydroxy-4-(3,4-dimethylphenoxy)-1-carbobenzyloxy-piperidine described in Example 19, 40.0 g (0.19 mol) of dicyclohexylcarbodiimide, 5.2 ml of pyridine and 4.2 g of trifluoroacetic acid in 130 ml of dry dimethylsulphoxide.

Hydrogenation, which is carried out analogously to Example 43 with 9.3 g (0.026 mol) of this product, gives crystalline 4-(3,4-dimethylphenoxy)-3-piperidone hydrochloride monohydrate; melting point 119°–120° (from methanol/acetone/ether).

EXAMPLE 45

Analogously to the procedure described in Example 43, 4-(2,3-dimethylphenoxy)-1-carbobenzyloxy-3-piperidone is obtained in the form of a colourless oil from 13.8 g (0.038 mol) of the trans-3-hydroxy-4-(2,3-dimethyl-phenoxy)-1-carbobenzyloxy-piperidine described in Example 34, 27.4 g (0.13 mol) of dicyclohexylcarbodiimide, 3.5 ml of pyridine and 1.9 ml of trifluoroacetic acid in 90 ml of dry dimethylsulphoxide; the oil can be crystallised from ethyl acetate to give a product with a melting point of 108°–111°.

Hydrogenation, which is carried out analogously to Example 46 with 4.75 g (0.013 mol) of this product, gives crystalline 4-(2,3-dimethylphenoxy)-3-piperidone hydrochloride monohydrate with a melting point of 110°–112°, after recrystallisation of the crude product from methanol/ether.

EXAMPLE 46

Analogously to the procedure described in Example 43, 3-(3,4-dimethyl-phenoxy)-1-carbobenzyloxy-4-piperidone is obtained in the form of a yellow oil from 28.3 g (0.08 mol) of the trans-4-hydroxy-3-(3,4-dimethylphenoxy)-1-carbobenzyloxy-piperidine described in Example 19, 7.0 ml of pyridine, 4.2 ml of trifluoroacetic acid and 56.2 g (0.27 mol) of dicyclohexylcarbodiimide in 180 ml of dry dimethylsulphoxide. For characterisation a sample was crystallised from ethyl acetate. Melting point 89°–90° C.

Hydrogenation, which is carried out analogously to Example 43 with 7.0 g (0.0198 mol) of this product, gives crystalline 3-(3,4-dimethyl-phenoxy)-4-piperidone hydrochloride monohydrate with a melting point of 127°–132° (from ethyl acetate/petroleum ether).

EXAMPLE 47

10.0 g (0.028 mol) of the 4-(3,4-dimethylphenoxy)-1-carbobenzyloxy-3-piperidone described in Example 44 are dissolved in 60 ml of dry tetrahydrofurane and the solution is treated dropwise, at room temperature in a nitrogen atmosphere, with 112 ml of a 0.5 M solution of potassium tri-sec.-butyl-borohydride (K selectride) (0.056 mol) in tetrahydrofurane. After the addition has ended, the reaction mixture is stirred for a further 3 hours at room temperature and then concentrated to about ⅓ of the original volume under a water pump vacuum. The solution is cooled to 0° in an ice-water bath, treated dropwise with 130 ml of water and extracted by shaking with twice 150 ml of methylene chloride. The combined organic phases are washed with 0.1 N hydrochloric acid, then with 0.1 N sodium hydroxide solution and finally with water, dried over a sodium sulphate and evaporated to dryness under a water pump vacuum. The oily crude product is dissolved in toluene and the solution is filtered through a layer of silica gel. cis-3-hydroxy-4-(3,4-dimethyl-phenoxy)-1-carbobenzyloxy-piperidine is obtained in the form of a pale yellow oil by elution with a toluene-/ethyl acetate mixture (5:1).

6.0 g (0.0168 mol) of this product are dissolved in 120 ml of methanol and hydrogenated in the presence of 0.6 g of a 5% strength palladium-on-charcoal catalyst under normal pressure and at room temperature. After the absorption of hydrogen has ceased, the catalyst is filtered off by means of diatomaceous earth and the filtrate is evaporated under a water pump vacuum. The resulting crude base, i.e. cis-3-hydroxy-4-(3,4-dimethyl-phenoxy)-piperidine, crystallises from methanol/ether; melting point 140°–143°. The neutral fumarate prepared therefrom with fumaric acid crystallises from methanol/ether; melting point 186°–190°.

EXAMPLE 48

Analogously to the procedure described in Example 47, cis-3-hydroxy-4-(2,3-dimethylphenoxy)-1-carbobenzyloxy-piperidine is obtained in the form of a yellowish oil from 8.0 g (0.022 mol) of the 4-(2,3-dimethylphenoxy)-1-carbobenzyloxy-3-piperidone described in Example 47, by selective reduction with potassium tri-sec.-butyl-borohydride.

Hydrogenation, which is carried out analogously to Example 47 with 3.7 g (0.01 mol) of this product, gives cis-3-hydroxy-4-(2,3-dimethylphenoxy)-piperidine in the form of a colourless oil. The neutral fumarate prepared therefrom with fumaric acid crystallises from methanol/ether; melting point 188°–189°.

EXAMPLE 49

6.64 g (0.03 mol) of the trans-3-hydroxy-4-(2,3-dimethyl-phenoxy)-piperidine described in Example 4 are dissolved in 100 ml of ethyl formate and the solution is boiled under reflux for 1½ hours. The cooled solution is evaporated to dryness under a water pump vacuum, the resulting white, solid residue is dissolved in 100 ml of methyl chloride and this solution is washed with 50 ml of 1 N hydrochloric acid, dried over sodium sulphate and evaporated to dryness under a water pump vacuum, trans-3-hydroxy-4-(2,3-dimethylphenoxy)-1-formyl-piperidine being obtained in the form of crystals with a melting point of 140°–141°.

In an analogous manner 4-trans-hydroxy-5-(2,3-dimethylphenoxy)-1-formyl-hexahydro-1H-azepine is obtained using 7.06 g (0.03 mol) of the 4-trans-hydroxy-5-(2,3-dimethyl-phenoxy)-hexahydro-1H-azepine described in Example 4.

7.5 g (0.03 mol) of the above 1-formyl compound are dissolved in 100 ml of dry tetrahydrofurane and this solution is added dropwise, in an inert nitrogen atmosphere at 0°, to a suspension of 2.0 g of lithium aluminium hydride in 150 ml of dry tetrahydrofurane. The reaction mixture is stirred for 5 hours at room temperature, then cooled to 0° again in an ice bath and treated successively with 2 ml of water, 2 ml of 2 N sodium hydroxide solution and 6 ml of water. The salts which have precipitated are filtered off and the filtrate is evaporated to dryness under a water pump vacuum. The colourless, oily residue is dissolved in 20 ml of chloroform and the solution is filtered through a layer of silica gel and the layer is washed (eluted) with further chloroform. The combined filtrates are evaporated under a water pump vacuum and crystalline trans-3-hydroxy-4-(2,3-dimethyl-phenoxy)-1-methyl-piperidine with a melting point of 105°–107° is obtained. The acid fumarate prepared from the base by treatment with fumaric acid crystallises from methanol/ether; melting point 150°–152°.

In an analogous manner trans-4-hydroxy-5-(2,3-dimethylphenoxy)-1-methyl-hexahydro-1H-azepine is obtained from 7.9 g (0.03 mol) of trans-4-hydroxy-5-(2,3-dimethyl-phenoxy)-1-formylhexahydro-1H-azepine.

EXAMPLE 50

Analogously to the procedure described in Example 49, cis-3-hydroxy-4-(2,3-dimethylphenoxy)-1-formyl-piperidine is obtained in the form of a pale yellow oil from 5.5 g (0.25 mol) of the cis-3-hydroxy-4-(2,3-dimethyl-phenoxy)-piperidine described in Example 48, by reaction in 100 ml of ethyl formate.

Reduction, which is carried out in a manner analogous to that in Example 49, with 3 g of lithium aluminium hydride in 100 ml of tetrahydrofurane gives cis-3-hydroxy-4-(2,3-dimethyl-phenoxy)-1-methyl-piperidine in the form of a colourless oil, which crystallises from methylene chloride; melting point 80°–82°. The neutral fumarate prepared from the base by treatment with fumaric acid crystallises from methanol/ether; melting point 159°–161°.

EXAMPLE 51

Analogously to the procedure described in Example 49, cis-3-hydroxy-4-(3,4-dimethylphenoxy)-1-formyl-piperidine is obtained as a yellowish oil from 5.2 g (0.023 mol) of the cis-3-hydroxy-4-(3,4-dimethyl-phenoxy)-piperidine described in Example 47, by reaction in 100 ml of ethyl formate.

Reduction, which is carried out analogously to Example 49, of this product (0.023 mol) with 3 g of lithium aluminium hydride in 150 ml of tetrahydrofurane gives cis-3-hydroxy-4-(3,4-dimethylphenoxy)-1-methyl-piperidine, which crystallises from methylene chloride; melting point 127°–129°. The fumarate prepared from the base by treatment with fumaric acid crystallises from ethanol/ether; melting point 157°–159°.

Likewise analogously to Example 46, trans-3-hydroxy-4-(naphthyloxy)-1-formyl-piperidine is obtained using 6.1 g (0.025 mol) of the trans-3-hydroxy-4-(1-naphthyloxy)-piperidine described in Example 10 and 100 ml of ethyl formate, and trans-3-hydroxy-4-(1-naphthyloxy)-1-methyl-piperidine is obtained in the form of a pale yellow oil by reduction of the above product (0.025 mol) with 3 g of lithium aluminium hydride in 150 ml of tetrahydrofurane. The hydrochloride prepared from the base using hydrogen chloride in ether is amorphous.

EXAMPLE 52

Analogously to Example 20, the 1-methyl derivatives corresponding to the compounds indicated below are obtained using, in each case, 0.04 mol of the indicated compounds, i.e. trans-3-hydroxy-4-(m-chlorophenoxy)-1-methyl-piperidine is obtained from 9.12 g of trans-3-hydroxy-4-(m-chlorophenoxy)-piperidine (Example 21), trans-3-hydroxy-4-phenylthio-1-methyl-piperidine is obtained from 8.36 g of trans-3-hydroxy-4-phenylthio-piperidine (Example 13), trans-3-hydroxy-4-(5,6,7,8-tetrahydro-1-naphthyloxy)-1-methyl-piperidine is obtained from 9.88 g of trans-3-hydroxy-4-(5,6,7,8-tetrahydro-1-naphthyloxy)-piperidine (Example 33), trans-3-hydroxy-4-(p-fluorophenoxy)-1-methyl-piperidine is obtained from 8.44 g of trans-3-hydroxy-4-(p-fluorophenoxy)-piperidone (Example 31), trans-3-acetoxy-4-(3,4-dimethyl-phenoxy)-1-methyl-piperidine is obtained from 10.60 g of trans-3-acetoxy-4-(3,4-dimethylphenoxy)-piperidine (Example 9), trans-3-hydroxy-4-(p-trifluoromethylphenoxy)-1-methyl-piperidine is obtained from 10.44 g of trans-3-hydroxy-4-(p-trifluoromethylphenoxy)-piperidine (Example 36), trans-4-hydroxy-5-(3,4-dimethyl-phenoxy)-1-methyl-hexahydro-1H-azepine and its hydrochloride are obtained from 9.40 g of trans-4-hydroxy-5-(3,4-dimethyl-phenoxy)-hexahydro-1H-azepine (Example 40), trans-4-hydroxy-5-(3,4-dichloro-phenoxy)-1-methyl-hexahydro-1H-azepine and its hydrochloride are obtained from 11.04 g of trans-4-hydroxy-5-(3,4-dichloro-phenoxy)-hexahydro-1H-azepine (Example 40) and trans-4-hydroxy-5-(p-trifluoromethyl-phenoxy)-1-methyl-hexahydro-1H-azepine and its hydrochloride are obtained from 11.0 g of trans-4-hydroxy-(p-trifluoromethyl-phenoxy)-hexahydro-1H-azepine (Example 40).

EXAMPLE 53

Analogously to Example 43, 4-(m-chloro-phenoxy)-1-carbobenzyloxy-3-piperidone is obtained from 16.3 g (0.045 mol) of trans-3-hydroxy-4-(m-chlorophenoxy)-1-carbobenzyloxy-piperidine (Example 21), and 4-(m-chlorophenoxy)-3-piperidone and its hydrochloride monohydrate are obtained from 14.4 g (0.04 mol) of the above piperidone; 4-(1-naphthyloxy)-1-carbobenzyloxy-3-piperidone is obtained from 17.0 g (0.045 mol) of trans-3-hydroxy-4-(1-naphthyloxy)-1-carbobenzyloxy-piperidine (Example 10), and 4-(1-naphthyloxy)-3-piperidone and its hydrochloride monohydrate are obtained from 15.0 g (0.04 mol) of the above piperidone; 4-(5,6,7,8-tetrahydro-1-naphthyloxy)-1-carbobenzyloxy-3-piperidone is obtained from 17.15 g (0.045 mol) of trans-3-hydroxy-4-(5,6,7,8-tetrahydro-1-naphthyloxy)-1-carbobenzyloxy-piperidine (Example 33), and 4-(5,6,7,8-tetrahydro-1-naphthyloxy)-3-piperidone and its hydrochloride monohydrate are obtained from 15.16 g (0.04 mol) of the above piperidone; 4-(p-fluorophenoxy)-1-carbobenzyloxy-3-piperidone is obtained from 15.5 g of trans-3-hydroxy-4-(p-fluorophenoxy)-1-carbobenzyloxy-piperidine (Example 31), and 4-(p-fluorophenoxy)-3-piperidone and its hydrochloride monohydrate are obtained from 13.72 g (0.04 mol) of the above piperidone; and 3-(3,4-dimethyl-phenoxy)-1-carbobenzyloxy-4-piperidone is obtained from 16.0 g of trans-4-hydroxy-3-(3,4-dimethyl-phenoxy)-1-carbobenzyloxy-piperidine (Example 19), and 3-(3,4-dimethyl-phenoxy)-4-piperidone and its hydrochloride monohydrate are obtained from 14.12 g (0.04 mol) of the above piperidone.

EXAMPLE 54

Analogously to Example 47, selective reduction and subsequent hydrogenolysis gives cis-3-hydroxy-4-(m-chloro-phenoxy)-piperidine from 10.2 g (0.028 mol) of 4-(m-chloro-phenoxy)-1-carbobenzyloxy-3-piperidone (Example 53), cis-3-hydroxy-4-(1-naphthyloxy)-piperidine from 10.5 g (0.028 mol) of 4-(1-naphthyloxy)-1-carbobenzyloxy-3-piperidone (Example 53), cis-3-hydroxy-4-(5,6,7,8-tetrahydro-1-naphthyloxy)-piperidine from 10.6 g (0.028 mol) of 4-(5,6,7,8-tetrahydro-1-naphthyloxy)-1-carbobenzyloxy-3-piperidone (Example 53), and cis-3-hydroxy-4-(p-fluorophenoxy)-piperidine from 9.6 g (0.028 mol) of 4-(p-fluoro-phenoxy)-1-carbobenzyloxy-3-piperidone (Example 53).

EXAMPLE 55

Analogously to Example 20, the 1-methyl derivatives corresponding to the compounds indicated below are obtained using, in each case, 0.02 mol of the indicated compounds, 10 ml of formic acid and 5 ml of a 35% strength aqueous solution of formaldehyde, i.e. cis-3-hydroxy-4-(m-chloro-phenoxy)-1-methyl-piperidine is obtained from 4.56 g of cis-3-hydroxy-4-(m-chlorophenoxy)-piperidine (Example 54), cis-3-hydroxy-4-(1-naphthyloxy)-1-methyl-piperidine is obtained from 4.86 g of cis-3-hydroxy-4-(1-napthyloxy)-piperidine (Example 54), cis-3-hydroxy-4-(5,6,7,8-tetrahydro-1-naphthyloxy)-1-methyl-piperidine is obtained from 4.94 g of cis-3-hydroxy-4-(5,6,7,8-tetrahydro-1-naphthyloxy)-piperidine (Example 54) and cis-3-hydroxy-4-(p-fluorophenoxy)-1-methyl-piperidine is obtained from 4.22 g of cis-3-hydroxy-4-(p-fluoro-phenoxy)-piperidine (Example 54).

EXAMPLE 56

Analogously to Example 24, etherification and subsequent hydrogenolysis using 1.35 g (0.03 mol) of a 55% strength oily dispersion of sodium hydride in 20 ml of dimethylformamide, 0.02 mol of the starting materials indicated below in 20 ml of dimethylformamide and 3.55 g (0.025 mol) of methyl iodide gives the corresponding end products, i.e. trans-3-methoxy-4-(2,3-dimethyl-phenoxy)-piperidine is obtained from 7.1 g of trans-3-hydroxy-4-(2,3-dimethyl-phenoxy)-1-carbobenzyloxy-piperidine (Example 34), cis-3-methoxy-4-(3,4-dimethyl-phenoxy)-piperidine is obtained from 7.1 g of cis-3-hydroxy-(3,4-dimethyl-phenoxy)-1-carbobenzyloxy-piperidine (Example 47) and cis-3-methoxy-4-(2,3-dimethyl-phenoxy)-piperidine is obtained from 7.1 g of cis-3-hydroxy-4-(2,3-dimethyl-phenoxy)-1-carbobenzyloxy-piperidine (Example 48).

EXAMPLE 57

Analogously to Example 20, the 1-methyl derivatives corresponding to the compounds indicated below are obtained using, in each case, 4.70 g (0.02 mol) of the indicated compounds (from Example 56), 10 ml of formic acid and 5 ml of a 35% strength aqueous solution of formaldehyde, i.e. trans-3-methoxy-4-(2,3-dimethyl-phenoxy)-1-methyl-piperidine is obtained from trans-3-methoxy-4-(2,3-dimethyl-phenoxy)-piperidine, cis-3-methoxy-4-(3,4-dimethyl-phenoxy)-1-methyl-piperidine is obtained from cis-3-methoxy-4-(3,4-dimethyl-phenoxy)-piperidine and cis-3-methoxy-4-(2,3-dimethyl-phenoxy)-1-methyl-piperidine is obtained from cis-3-methoxy-4-(2,3-dimethyl-phenoxy)-piperidine.

EXAMPLE 58

A solution of 15.0 g (0.04 mol) of the trans-3-hydroxy-4-(3,4-dimethyl-phenoxy)-1-carbobenzyloxy-piperidine described in Example 19 in 100 ml of dimethylformamide is introduced in the course of 30 minutes, at 30°-35°, into a suspension of 2.8 g (0.062 mol) of a 55% strength oily dispersion of sodium hydride in 50 ml of dimethylformamide. The mixture is then warmed to 50° and treated dropwise with 7.16 g (0.055 mol) of 1-chloro-3-fluorobenzene. The reaction mixture is subsequently stirred for 4½ hours at 60°–70° and then for 15 hours at room temperature, cooled in an ice-water bath and treated with 250 ml of water. The mixture is extracted by shaking with 3 times 250 ml of ethyl acetate and the combined organic phases are washed twice with water, dried over magnesium sulphate and evaporated to dryness, first under a water pump vacuum and then under a high vacuum. The oil which remains behind is dissolved in 100 ml of toluene and the solution is filtered through a layer of silica gel. Elution with a toluene-/ethyl acetate mixture (4:1) gives trans-3-(3-chlorophenoxy)-4-(3,4-dimethylphenoxy)-1-carbobenzyloxy-piperidine in the form of a pale yellow oil.

5.4 g (0.011 mol) of this compound are dissolved in 120 ml of methanol and the solution is treated with 3.3 ml of a 2.5 N methanolic solution of hydrogen chloride and hydrogenated in the presence of 1.8 g of a 5% strength palladium-on-charcoal catalyst under normal pressure and at room temperature. After the absorption of hydrogen has ceased, the catalyst is filtered off over diatomaceous earth and the filtrate is evaporated under a water pump vacuum. The base is set free from the crude hydrochloride by treatment with aqueous ammonia solution and extracted with methylene chloride. After evaporation of the methylene chloride solution, which has been dried over sodium sulphate, trans-3-(3-chloro-phenoxy)-4-(3,4-dimethyl-phenoxy)-piperidine is obtained in the form of a pale yellow oil. The acid fumarate prepared with fumaric acid crystallises from methanol/ether; melting point 148°–150°.

EXAMPLE 59

Tablets weighing 100 mg and containing 20 mg of active compound are prepared in the following composition in the customary manner:

| Composition | |
|---|---|
| Trans-3-hydroxy-4-(2,3-dimethyl-phenoxy)-piperidine fumarate (2:1) (neutral) | 27 mg |
| Wheat starch | 50 mg |
| Lactose | 43 mg |
| Colloidal silica | 5 mg |
| Talc | 9 mg |
| Magnesium stearate | 1 mg |
| | 135 mg |

Preparation

The trans-3-hydroxy-4-(2,3-dimethyl-phenoxy)-piperidine fumarate (2:1) is mixed with a portion of the wheat starch and with the lactose and colloidal silica and the mixture is forced throubh a sieve. A further portion of the wheat starch is mixed to a paste with 5 times the amount of water on a water bath and the pulverulent mixture is kneaded with this paste until a slightly plastic mass has formed.

The plastic mass is pressed through a sieve of about 3 mm mesh width and dried and the resulting dry granules are again forced through a sieve. The remainder of the wheat starch, the talc and the magnesium stearate are then mixed in and the mixture is pressed to give tablets weighing 135 mg with a breaking groove.

EXAMPLE 60

Tablets weighing 100 mg and containing 20 mg of trans-3-hydroxy-4-(3,4-dimethyl-phenoxy)-1-methyl-piperidine hydrochloride as the active compound are prepared analogously to the procedure described in Example 59.

What I claim is:

1. A compound of the formula

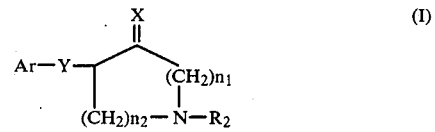

wherein X is hydrogen and the radical OR$_1$, in which R$_1$ is hydrogen, lower alkyl or an acyl group —C(=O)—R, in which R is lower alkyl, R$_2$ is hydrogen, lower alkyl, lower alkenyl or lower alkinyl, Ar is phenyl, naphthyl or 5,6,7,8-tetrahydronaphthyl, which are unsubstituted or mono- or disubstituted in an aromatic ring, at most two substituents being selected from lower alkyl, lower alkoxy and halogen, and at most one substituent being selected from trifluoromethyl, carbamoyl, nitro and cyano, Y is oxygen, n$_1$ and n$_2$ are each one, or an acid addition salt thereof.

2. A compound according to claim 1, in which X is hydrogen and the radical OR$_1$, in which R$_1$ is hydrogen, lower alkyl or an acyl group —C(=O)—R, in which R is lower alkyl, R$_2$ is hydrogen, lower alkyl or propargyl, Ar is phenyl, naphthyl or 5,6,7,8-tetrahydronaphthyl, and phenyl is unsubstituted or mono- or disubstituted by lower alkyl, lower alkoxy or halogen, or substituted by trifluoromethyl, said substituents being identical or different from one another, Y is oxygen, n$_1$ and n$_2$ are each one, or an acid addition salt thereof.

3. A compound according to claim 1, which is trans-3-hydroxy-4-phenoxy-pyrrolidine or a pharmaceutically acceptable acid addition salt thereof.

4. A compound according to claim 1, which is trans-3-hydroxy-4-(4-carbamoyl-phenoxy)-pyrrolidine or a pharmaceutically acceptable acid addition salt thereof.

5. A compound according to claim 1, which is trans-3-hydroxy-4-(4-methoxy-phenoxy)-pyrrolidine or a pharmaceutically acceptable acid addition salt thereof.

6. A compound according to claim 1, which is trans-3-hydroxy-4-(1-naphthyloxy)-pyrrolidine or a pharmaceutically acceptable acid addition salt thereof.

7. A compound according to claim 1, which is trans-3-hydroxy-4-(2-methyl-phenoxy)-pyrrolidine or a pharmaceutically acceptable acid addition salt thereof.

8. A compound according to claim 1, which is trans-3-hydroxy-4-(3,4-dimethyl-phenoxy)-pyrrolidine or a pharmaceutically acceptable acid addition salt thereof.

9. A compound according to claim 1, which is trans-3-acetoxy-4-(3,4-dimethyl-phenoxy)-pyrrolidine or a pharmaceutically acceptable acid addition salt thereof.

10. A compound according to claim 1, which is trans-3-hydroxy-4-(3-chlorophenoxy)-pyrrolidine or a pharmaceutically acceptable acid addition salt thereof.

11. A compound according to claim 1, which is trans-3-hydroxy-4-(3,5-dimethyl-phenoxy)-pyrrolidine or a pharmaceutically acceptable acid addition salt thereof.

12. A pharmaceutical composition for the treatment of mental depression comprising a therapeutically effective amount of a compound of the formula

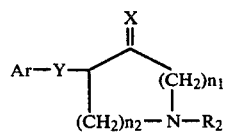

(I)

wherein X is hydrogen and the radical OR$_1$, in which R$_1$ is hydrogen, lower alkyl or an acyl group —C(=O)—R, in which R is lower alkyl, R$_2$ is hydrogen, lower alkyl, lower alkenyl or lower alkinyl, Ar is phenyl, naphthyl or 5,6,7,8-tetrahydronaphthyl which are unsubstituted or mono- or disubstituted in an aromatic ring, at most two substituents being selected from lower alkyl, lower alkoxy, and halogen, and at most one substituent being selected from trifluoromethyl, carbamoyl, nitro and cyano, said substituents being identical or different from one another, Y is oxygen, n$_1$ and n$_2$ are each one, or a pharmaceutically acceptable acid addition salt thereof together with a pharmaceutical excipient.

13. A pharmaceutical composition according to claim 12, wherein a therapeutically effective amount of a compound of formula I given in claim 12, in which X is hydrogen, lower alkyl or an acyl group —C(=O)—R, in which R is lower alkyl, R$_2$ is hydrogen, lower alkyl or propargyl, Ar is Phenyl, naphthyl or 5,6,7,8-tetrahydronaphthyl, and phenyl is unsubstituted or mono- or disubstituted by lower alkyl, lower alkoxy or halogen, or substituted by trifluoromethyl, said substituents being identical or different from one another, Y is oxygen, n$_1$ and n$_2$ are each one, or a pharmaceutically acceptable acid addition salt thereof, together with a pharmaceutical excipient, is present.

14. A pharmaceutical composition according to claim 12, wherein a therapeutically effective amount of 3-hydroxy-4-(3,4-dimethyl-phenoxy)-pyrrolidine or of a pharmaceutically acceptable acid salt thereof, together with a pharmaceutical excipient, is present.

15. A pharmaceutical composition according to claim 12, wherein a therapeutically effective amount of 3-hydroxy-4-(1-naphthyloxy)-pyrrolidine or of a pharmaceutically acceptable acid addition salt thereof, together with a pharmaceutical excipient, is present.

16. A method for the treatment of mental depression in a warm-blooded animal comprising enteral or parenteral administration to said animal of a therapeautically, effective amount of a compound according to claim 1, having the formula 1 defined in claim 1, or of a pharmaceutically acceptable acid addition salt thereof.

* * * * *